United States Patent
Orlandi et al.

(10) Patent No.: US 9,717,710 B2
(45) Date of Patent: Aug. 1, 2017

(54) TREATMENT OF MILD AND MODERATE ALZHEIMER'S DISEASE

(71) Applicant: vTv Therapeutics LLC, High Point, NC (US)

(72) Inventors: Cesare Orlandi, Boston, MA (US); David J. Clark, Winchester, MA (US); Imogene M. Dunn, Greensboro, NC (US); Maria Carmen Valcarce Lopez, Oak Ridge, NC (US); Matthew J. Kostura, Hillsborough, NC (US)

(73) Assignee: vTv THERAPEUTICS LLC, High Point, NC (US)

( * ) Notice: Subject to any disclaimer, the term of this patent is extended or adjusted under 35 U.S.C. 154(b) by 371 days.

(21) Appl. No.: 14/059,529

(22) Filed: Oct. 22, 2013

(65) Prior Publication Data

US 2014/0100218 A1   Apr. 10, 2014

Related U.S. Application Data

(63) Continuation of application No. PCT/US2013/062964, filed on Oct. 2, 2013.

(60) Provisional application No. 61/710,229, filed on Oct. 5, 2012.

(51) Int. Cl.
  *A61K 31/4164* (2006.01)
  *A61K 45/06* (2006.01)
  *A61K 31/13* (2006.01)

(52) U.S. Cl.
  CPC .......... *A61K 31/4164* (2013.01); *A61K 31/13* (2013.01); *A61K 45/06* (2013.01)

(58) Field of Classification Search
  None
  See application file for complete search history.

(56) References Cited

U.S. PATENT DOCUMENTS

| | | | |
|---|---|---|---|
| 5,011,849 A | 4/1991 | Gassner et al. | |
| 5,166,214 A | 11/1992 | Billheimer et al. | |
| 5,585,344 A | 12/1996 | Vlassara et al. | |
| 5,817,626 A | 10/1998 | Findeis et al. | |
| 5,840,294 A | 11/1998 | Kisilevsky et al. | |
| 5,864,018 A | 1/1999 | Morser et al. | |
| 5,922,770 A | 7/1999 | Peschke et al. | |
| 5,939,526 A | 8/1999 | Gaugler et al. | |
| 5,962,535 A | 10/1999 | Miyamoto et al. | |
| 6,221,667 B1 | 4/2001 | Reiner et al. | |
| 6,268,479 B1 | 7/2001 | Stern et al. | |
| 6,274,615 B1 | 8/2001 | Pappolla et al. | |
| 6,323,218 B1 | 11/2001 | Bush et al. | |
| 6,441,049 B2 | 8/2002 | Reitz et al. | |
| 6,472,145 B2 | 10/2002 | Reiner et al. | |
| 6,613,801 B2 | 9/2003 | Mjalli et al. | |
| 6,677,299 B2 | 1/2004 | Stern et al. | |
| 6,825,164 B1 | 11/2004 | Stern et al. | |
| 7,067,554 B2 | 6/2006 | Mjalli et al. | |
| 7,087,632 B2 | 8/2006 | Mjalli et al. | |
| 7,329,684 B2 | 2/2008 | Mjalli et al. | |
| 7,361,678 B2* | 4/2008 | Mjalli .................. | C07D 233/64 514/397 |
| 7,421,177 B2 | 9/2008 | Schmidt et al. | |
| 7,423,177 B2 | 9/2008 | Mjalli et al. | |
| 7,714,013 B2 | 5/2010 | Mjalli et al. | |
| 7,737,285 B2 | 6/2010 | Mjalli et al. | |
| 7,776,919 B2 | 8/2010 | Mjalli et al. | |
| 7,884,219 B2* | 2/2011 | Hari ..................... | C07D 233/60 548/470 |
| 8,372,988 B2 | 2/2013 | Hari | |
| 8,580,833 B2 | 11/2013 | Jones et al. | |
| 2001/0039256 A1 | 11/2001 | Stern et al. | |
| 2002/0006957 A1 | 1/2002 | Mjalli et al. | |
| 2002/0116725 A1 | 8/2002 | Stern et al. | |
| 2002/0122799 A1 | 9/2002 | Stern et al. | |
| 2002/0193432 A1 | 12/2002 | Mjalli et al. | |
| 2003/0032663 A1 | 2/2003 | Mjalli et al. | |
| 2004/0063770 A1 | 4/2004 | Ahn et al. | |
| 2004/0082542 A1 | 4/2004 | Mjalli et al. | |
| 2004/0097407 A1 | 5/2004 | Mjalli et al. | |
| 2005/0026811 A1 | 2/2005 | Mjalli et al. | |
| 2006/0020042 A1 | 1/2006 | McDonald et al. | |
| 2006/0247253 A1 | 11/2006 | Leban et al. | |
| 2007/0021386 A1 | 1/2007 | Mjalli et al. | |
| 2007/0135437 A1 | 6/2007 | Benjamin et al. | |
| 2009/0035302 A1 | 2/2009 | Mjalli et al. | |

(Continued)

FOREIGN PATENT DOCUMENTS

WO   WO 95/09838 A1   4/1995
WO   WO 97/26913 A1   7/1997

(Continued)

OTHER PUBLICATIONS

Investor Presentation—Jul. 2015, slides 9-18.*
Burnstein et al., Evaluation of the relationship between TTP448 plasma concentration and changes in ADAS-cog relative to placebo, Poster session presented at: the Alzheimer's Association International Conference, Jul. 13-18, 2013, Boston, Massachusetts.*
Sabbagh et al., PF-04494700, an Oral Inhibitor of Receptor for Advanced Glycation End Products (RAGE), in Alzheimer's disease, Alzheimer Dis Assoc Disord. Jul.-Sep. 2011; 25(3): 206-212.*
Mangialasche, Alzheimer's disease: clinical trials and drug development, The Lancet Neurology, vol. 9, Issue 7, Jul. 2010, pp. 702-716.*

(Continued)

*Primary Examiner* — Svetlana M Ivanova

(74) *Attorney, Agent, or Firm* — Wilmer Cutler Pickering Hale and Dorr LLP

(57) ABSTRACT

The present invention relates to methods of treatment using [3-(4-{2-butyl-1-[4-(4-chloro-phenoxy)-phenyl]-1H-imidazol-4-yl}-phenoxy)-propyl]-diethyl amine ("COMPOUND I") or a pharmaceutically acceptable salt thereof. In various embodiments, the methods of treatment include treatment of mild-to-moderate dementia of Alzheimer's type, diabetes, insomnia, and other indications. The present invention also relates to pharmaceutical compositions comprising COMPOUND I or a pharmaceutically acceptable salt thereof.

22 Claims, 14 Drawing Sheets

(56) References Cited

U.S. PATENT DOCUMENTS

| | | |
|---|---|---|
| 2010/0048726 A1 | 2/2010 | McDonald et al. |
| 2010/0256119 A1 | 10/2010 | Mjalli et al. |
| 2012/0088778 A1 | 4/2012 | Mjalli et al. |
| 2014/0039025 A1 | 2/2014 | Jones et al. |

FOREIGN PATENT DOCUMENTS

| | | | |
|---|---|---|---|
| WO | WO 97/39121 A1 | 10/1997 | |
| WO | WO 97/39125 A1 | 10/1997 | |
| WO | WO 98/22138 A1 | 5/1998 | |
| WO | WO 99/07402 A1 | 2/1999 | |
| WO | WO 99/18987 A1 | 4/1999 | |
| WO | WO 99/54485 A1 | 10/1999 | |
| WO | WO 00/19994 A1 | 4/2000 | |
| WO | WO 00/20458 A1 | 4/2000 | |
| WO | WO 00/20621 A1 | 4/2000 | |
| WO | WO 01/12598 A2 | 2/2001 | |
| WO | WO 01/92210 A1 | 12/2001 | |
| WO | WO 02/069965 A1 | 9/2002 | |
| WO | WO 02/070473 A2 | 9/2002 | |
| WO | WO 03/075921 | 9/2003 | |
| WO | WO 2004/087653 A2 | 10/2004 | |
| WO | WO 2004/110350 A2 | 12/2004 | |
| WO | WO 2005/000295 A1 | 1/2005 | |
| WO | WO 2005000295 A1 * | 1/2005 | ......... A61K 31/4164 |
| WO | WO 2006/124897 A2 | 11/2006 | |
| WO | WO 2008/067121 A2 | 6/2008 | |
| WO | WO 2008/153957 A1 | 12/2008 | |
| WO | WO 2010/126745 A1 | 11/2010 | |
| WO | WO 2011/103091 A1 | 8/2011 | |

OTHER PUBLICATIONS

Galasko et al., "A Randomized Clinical Trial of an Inhibitor of RAGE-AP Interactions in Patients with Mild to Moderate AD," Draft of presentation Presented at Clinical Trials on Alzheimer's Disease program, San Diego, California, Nov. 3, 2011.*
Amendment No. 6 to Form S-1 Registration Statement for vTv Therapeutics Inc., Jul. 24, 2015. pp. 1-2, 83, 86-94.
ARICEPT® package insert, Feb. 2012.
Bonetta, "Door Slams on RAGE," Alzheimer Research Forum Print News, Nov. 9, 2011.
Burstein et al. "Evaluation of the relationship between TTP488 plasma concentration and changes in ADAS-cog relative to placebo." Poster session presented at: the Alzheimer's Association International Conference, Jul. 13-18, Boston, Massachusetts, 2013.
Burstein et al., "Effect of TTP488 in patients with mild to moderate Alzheimer's disease," BMC Neurology 14:12 (2014), 19 pages.
Burstein et al., "Evaluation of the relationship between TTP488 plasma concentrations and changes in ADAS-cog relative to placebo." Abstract presented Jul. 14, 2013 at: the Alzheimer's Association International Conference, Jul. 13-18, 2013, Boston, Massachusetts.
Davis, et al., "RAGE Deletion Increases Anti-Oxidant and Anti-Inflammatory Biochemical Profiles in Human APP Transgenic Mice," Poster presented at Alzheimer's Association International Conference, Washington, DC, Jul. 20, 2015.
Galasko et al., "A clinical trial of an inhibitor of RAGE-A-beta interactions in Alzheimer's disease," RI clinical trial manuscript, Aug. 8, 2012.
Galasko et al., "A Randomized Clinical Trial of an inhibitor of RAGE-A-beta interactions in patients with mild to moderate AD," Draft of presentation in Clinical Trials on Alzheimer's Disease program, San Diego, California, Nov. 3, 2011.
Galasko et al., "Clinical trial of an inhibitor of RAGE-A-beta interactions in Alzheimer disease," Neurology 82:1537-1542 (2014).
Galasko et al., Supplements 1-6 to "Clinical trial of an inhibitor of RAGE-A-beta interactions in Alzheimer disease," Neurology 82:1537-1542 (2014).

International Search Report and Written Opinion for related International Applicaton No. PCT/US2013/062964, mailed Nov. 19, 2013.
Investor Presentation—Jul. 2015. Slides 9-18.
Kostura et al. Efficacy of RAGE antagonist in murine model of Alzheimer's disease. Poster session presented at: the Alzheimer's Association International Congress; Jul. 13-18, 2014; Cophenhagen, Denmark.
Namenda® package insert, 2007, Jan. 2011.
Perrone et al., "The Complexity of Sporadic Alzheimer's Disease Pathogenesis: The Role of RAGE as Therapeutic Target to Promote Neuroprotection by Inhibiting Neurovascular Dysfunction," International Journal of Alzheimer's Disease, vol. 2012, 13 pages.
Sabbagh, M., "Evaluation of Phase 2b Safety of Azeliragon (TTP488)" presented at Clinical Trials on Alzheimer's Disease program, Barcelona, Spain, Nov. 6, 2015.
Barile et al., "The RAGE Axis in Early Diabetic Retinopathy," Investigative Opththalmology & Visual Science 46(8):2916-2924 (2005).
Behl et al., "Amyloid beta peptide induces necrosis rather than apoptosis." Brain Research 645:253-264 (1994).
Behl et al., "Hydrogen Peroxide Mediates Amyloid beta Protein Toxicity," Cell 77:817-827 (1994).
Berge et al., "Pharmaceutical Salts," Journal of Pharmaceutical Sciences 66(1):1-19 (1977).
Bierhaus et al., "Advanced Glycation End Product (AGE)-Mediated Induction of Tissue Factor in Cultured Endothelial Cells is Dependent on RAGE," Circulation 96:2262-2271 (1997).
Bishop et al., "Neural mechanisms of ageing and cognitive decline," Nature 464:529-535 (2010).
Blacker et al., "Reliability and Validity of NINCDS-ADRDA Criteria for Alzheimer's Disease," Arch. Neurol. 51:1198-1204 (1994).
Bonnardel-Phu et al., "Acute Modulation of Albumin Microvascular Leakage by Advanced Glycation End Products in Microcirculation of Diabetic Rats In Vivo," Diabetes 48:2052-2058 (1999).
Burstein A, et al. "Azeliragon Phase 2b Survival Analysis Supports Beneficial Effects on Delaying Time to Cognitive Deterioration in Patients with Mild Alzheimer's Disease." Poster Presented at the Alzheimer's Association International Conference. Jul. 27, 2016. Toronto, Canada.
Chartier-Harlin et al., "Early-onset Alzheimer's disease caused by mutations at codon 717 of the beta-amyloid precursor protein gene," Nature 353:844-846 (1991).
Checler, "Processing of the beta-Amyloid Precursor Protein and Its Regulation in Alzheimer's Disease," Journal of Neurochemistry 65(4):1431-1444 (1995).
Chitaley et al., "Antagonism of Rho-kinase stimulates rat penile erection via a nitric oxide-independent pathway," Nature Medicine 7(1):119-122 (2001).
Crall, Jr. et al., "The Extramural and Intramural Coronary Arteries in Juvenile Diabetes Mellitus," The American Journal of Medicine 64:221-230 (1978).
Deane et al., "RAGE mediates amyloid-beta peptide transport across the blood-brain barrier and accumulation in brain," Nature Medicine 9(7):907-913 (2003).
Degenhardt et al., "Chemical Modification of Proteins by Methylglyoxal," Cellular and Molecular Biology 44(7):1139-1145 (1998).
Donahue et al., "RAGE, LRP-1, and amyloid-beta protein in Alzheimer's disease," Acta Neuropathol. 112:405-415 (2006).
Dyer et al., "Accumulation of Maillard Reaction Products in Skin Collagen in Diabetes and Aging," J. Clin. Invest. 91:2463-2469 (1993).
Dyer et al., "Formation of Pentosidine during Nonenzymatic Browning of Proteins by Glucose," The Journal of Biological Chemistry 266(18):11654-11660 (1991).
Fang et al., "RAGE-dependent signaling in microglia contributes to neuroinflammation, A-beta accumulation, and impaired learning/memory in a mouse model of Alzheimer's disease," The FASEB Journal 24:1043-1055 (2010).
G. Basta et al., 63 Cardiovascular Research 582-592 (2004).
G.P. Sims et al., 28 Annual Review of Immunology, 367-368 (2010).

(56) References Cited

OTHER PUBLICATIONS

Galasko et al., "Clinical-Neuropathological Correlations in Alzheimer's Disease and Related Dementias," Arch. Neurol. 51:888-895 (1994).
Games et al., "Alzheimer-type neuopathology in transgenic mice overexpressing V717F beta-amyloid precursor protein," Nature 373:523-527 (1995).
Girouard et al., "Neurovascular coupling in the normal brain and in hypertension, stroke, and Alzheimer disease," J. Appl. Physiol. 100:328-335 (2006).
Golub et al., "Molecular Classification of Cancer: Class Discovery and Class Prediction by Gene Expression Monitoring," Science 286:531-537 (1999).
Goova et al., "Blockade of Receptor for Advanced Glycation End-Products Restores Effective Wound Healing in Diabetic Mice," The American Journal of Pathology 159:513-525 (2001).
Haass et al., "Cellular Processing of beta-Amyloid Precursor Protein and the Genesis of Amyloid beta-Peptide," Cell 75:1039-1042 (1993).
Hambly et al., "Reappraisal of the role of the diabetic state in coronary artery disease," Chest 70(2):251-257 (1976).
Hammes et al., "Diabetic retinopathy risk correlates with intracellular concentrations of the glycoxidation product N(epsilon)-(carboxymethyl) lysine independently of glycohaemoglobin concentrations," Diabetologia 42:603-607 (1999).
Hofmann et al., "RAGE Mediates a Novel Proinflammatory Axis: A Central Cell Surface Receptor for S100/Calgranulin Polypeptides," Cell 97:889-901 (1999).
Hori et al., "The Receptor for Advanced Glycation End Products (RAGE) Is a Cellular Binding Site for Amphoterin," The Journal of Biological Chemistry 270(43):25752-25761 (1995).
Huttunen et al., "Receptor for Advanced Glycation End Products (RAGE)-mediated Neurite Outgrowth and Activation of NF-κB Require the Cytoplasmic Domain of the Receptor but Different Downstream Signaling Pathways," The Journal of Biological Chemistry 274(28):19919-19924 (1999).
Johnson et al., "MDL 29311: Antioxidant With Marked Lipid- and Glucose-Lowering Activity in Diabetic Rats and Mice," Diabetes 42:1179-1186 (1993).
Kamboh, "Molecular Genetics of Late-Onset Alzheimer's Disease," Annals of Human Genetics 68:381-404 (2004).
Kannel et al., "Diabetes and Cardiovascular Disease: The Framingham Study," JAMA 241(19):2035-2038 (1979).
Kannel et al., "Diabetes and Glucose Tolerance as Risk Factors for Cardiovascular Disease: The Framingham Study," Diabetes Care 2(2):120-126 (1979).
Kennedy et al., "Familial Alzheimer's disease," Brain 116:309-324 (1993).
Kislinger et al., "Receptor for Advanced Glycation End Products Mediates Inflammation and Enhanced Expression of Tissue Factor in Vasculature of Diabetic Apolipoprotein E-Null Mice," Arterioscler Thromb Vasc Biol. 21:905-910 (2001).
Kumar et al., "RAGE at the Blood-Brain Barrier Mediates Neurovascular Dysfunction Caused by Amyloid-beta1-40 Peptide," Neurosci. Program, p. 141-#275.19 (2000).
Lander et al., "Activation of the Receptor for Advanced Glycation End Products Triggers a p21(ras)-dependent Mitogen-activated Protein Kinase Pathway Regulated by Oxidant Stress," The Journal of Biological Chemistry 272(28):17810-17814 (1997).
Levy-Lahad et al., "Candidate Gene for the Chromosome 1 Familial Alzheimer's Disease Locus," Science, New Series 269(5226):973-977 (1995).
Li et al., "Characterization and Functional Analysis of the Promoter of RAGE, the Receptor for Advanced Glycation End Products," The Journal of Biological Chemistry 272(26):16498-16506 (1997).
Li et al., "Sp1-binding Elements in the Promoter of RAGE Are Essential for Amphoterin-mediated Gene Expression in Cultured Neuroblastoma Cells," The Journal of Biological Chemistry 273:30870-30878 (1998).
Mackic et al., "Human Blood-Brain Barrier Receptors for Alzheimer's Amyloid-beta 1-40: Asymmetrical Binding, Endocytosis, and Transcytosis at the Apical Side of Brain Microvascular Endothelial Cell Monolayer," J. Clin. Invest. 102(4):734-743 (1998).
McKhann et al., "Clinical diagnosis of Alzheimer's disease: Report of the NINCDS-ADRDA Work Group under the auspices of Department of Health and Human Services Task Force on Alzheimer's Disease," Neurology 34:939-944 (1984).
Miyata et al., "Beta2-Microglobulin Modified with Advanced Glycation End Products Is a Major Component of Hemodialysis-associated Amyloidosis," J. Clin. Invest. 92:1243-1252 (1993).
Miyata et al., "The Receptor for Advanced Glycation End Products (RAGE) Is a Central Mediator of the Interaction of AGE-beta2Microglobulin with Human Mononuclear Phagocytes Via an Oxidant-sensitive Pathway," J. Clin. Invest. 98(5):1088-1094 (1996).
Morcos et al., "Activation of Tubular Epithelial Cells in Diabetic Nephropathy," Diabetes 51:3532-3544 (2002).
Morris et al., "Place navigation impaired in rats with hippocampal lesions," Nature 297:681-683 (1982).
Neeper et al., "Cloning and Expression of a Cell Surface Receptor for Advanced Glycosylation End Products of Proteins," The Journal of Biological Chemistry 267(21):14998-15004 (1992).
Ohkubo et al., "Studies on Cerebral Protective Agents. VII. Synthesis of Novel 4-Arylazole Derivatives with Anti-anoxic Activity," Chem. Pharm. Bull. 43(6):947-954 (1995).
Oldfield et al., "Advanced glycation end products cause epithelial-myofibroblast transdifferentiation via the receptor for advanced glycation end products (RAGE)," The Journal of Clinical Investigation 108(12):1853-1863 (2001).
Pappolla et al., "The Heat Shock/Oxidative Stress Connection: Relevance to Alzheimer Disease," Molecular and Chemical Neuropathology 28:21-24 (1996).
Park et al., "Suppression of accelerated diabetic atherosclerosis by the soluble receptor for advanced glycation endproducts," Nature Medicine 4(9):1025-1031 (1998).
Parkkinen el al., "Amphoterin, the 30-kDa Protein in a Family of HMG1-type Polypeptides, Enhanced Expression in Transformed Cells, Leading Edge Localization, and Interactions with Plasminogen Activation," The Journal of Biological Chemistry 268(26):19726-19738 (1993).
Pastor et al., "Molecular Genetics of Alzheimer's Disease," Current Psychiatry Reports 6:125-133 (2004).
Pike et al., "Neurodegeneration Induced by beta-Amyloid Peptides in vitro: The Role of Peptide Assembly State," The Journal of Neuroscience 13(4):1676-1687 (1993).
Porretta et al., "Chemotherapeutic agents with an imidazole moiety. III. Synthesis and microbiological activity of new 1,4-diaryl-limidazole and 1,4-pyrrolimidazolephenylene derivatives," Il Farmaco 46(7,8):913-924 (1991).
Pyorala et al., "Diabetes and Atherosclerosis: An Epidemiologic View," Diabetes/Metabolism Reviews 3(2):463-524 (1987).
R. Ramasamy (YAN) et al., 15 Glycobiology 16R-18R (2005).
Rammes et al., "Myeloid-related Protein (MRP) 8 and MRP14, Calcium-binding Proteins of the S100 Family, Are Secreted by Activated Monocytes via a Novel, Tubulin-dependent Pathway," The Journal of Biological Chemistry 272(14):9496-9502 (1997).
Ranginwala et al., "Clinical Criteria for the Diagnosis of Alzheimer Disease: Still Good After All These Years," Am. J. Geriatr. Psychiatry 16(5):384-388 (2008).
Rauvala et al., "Isolation and Some Characteristics of an Adhesive Factor of Brain That Enhances Neurite Outgrowth in Central Neurons," The Journal of Biological Chemistry 262(34):16625-16635 (1987).
Reddy et al., "N(epsilon)-(Carboxymethyl)lysine Is a Dominant Advanced Glycation End Product (AGE) Antigen in Tissue Proteins," Biochemistry 34:10872-10878 (1995).
Ritthaler et al., "Expression of Receptors for Advanced Glycation End Products in Peripheral Occlusive Vascular Disease," American Journal of Pathology 146(3):688-694 (1995).
Robertson et al., "Atherosclerosis in persons with Hypertension and Diabetes Mellitus," Laboratory Investigation 18(5):538-551 (1968).

(56) References Cited

OTHER PUBLICATIONS

Rogaev et al., "Familial Alzheimer's disease in kindreds with missense mutations in a gene on chromosome 1 related to the Alzheimer's disease type 3 gene," Nature 376:775-778 (1995).
Sabbagh et al., "PF-04494700, an Oral Inhibitor of Receptor for Advanced Glycation End Products (RAGE), in Alzheimer Disease," Alzheimer Disease & Associated Disorders 25(3):206-212 (2011).
Schafer et al., "The S100 family of EF-hand calcium-binding proteins: functions and pathology," TIBS 21:134-140 (1996).
Schleicher et al., "Increased Accumulation of the Glycoxidation Product N(epsilon)-(carboxymethyl)lysine in Human Tissues in Diabetes and Aging," J. Clin. Invest. 99(3):457-468 (1997).
Schmidt et al., "Advanced Glycation Endproducts Interacting with Their Endothelial Receptor Induce Expression of Vascular Cell Adhesion Molecule-1 (VCAM-1) in Cultured Human Endothelial Cells and in Mice," J. Clin. Invest. 96:1395-1403 (1995).
Schmidt et al., "Isolation and Characterization of Two Binding Proteins for Advanced Glycosylation End Products from Bovine Lung Which Are Present on the Endothelial Cell Surface," The Journal of Biological Chemistry 267(21):14987-14977 (1992).
Schmidt et al., "Receptor for advanced glycation end products (AGEs) has a central role in vessel wall interactions and gene activation in response to circulating AGE proteins," Proc. Natl. Acad. Sci. USA 91:8807-8811 (1994).
Schmidt et al., "The dark side of glucose," Nature Medicine 1(10):1002-1004 (1995).
Schmidt et al., "The role of RAGE in amyloid-beta peptide-mediated pathology in Alzheimer's disease," Current Opinion in Investigational Drugs 10(7):672-680 (2009).
Schmidt et al., "The V-Domain of Receptor for Advanced Glycation Endproducts (RAGE) Mediates Binding of AGEs: A Novel Target for Therapy of Diabetic Complications," Supplement to Circulation 96(8):Abstract No. 194 (1997).
Selkoe, "Normal and Abnormal Biology of the beta-Amyloid Precursor Protein," Annual Review of Neuroscience 17:489-517 (1994).
Selkoe, "The Molecular Pathology of Alzheimer's Disease," Neuron 6:487-498 (1991).
Selkoe, "Translating cell biology into therpeutic advances in Alzheimer's disease," Nature 399:A23-31 (1999).
Semprini et al., "Evidence for differential S100 gene over-expression in psoriatic patients from genetically heterogeneous pedigrees," Hum. Genet. 111:310-313 (2002).
Sherrington et al., "Cloning of a gene bearing missense mutations in early-onset familial Alzheimer's disease," Nature 375:754-760 (1995).
Snowdon, "Healthy Aging and Dementia: Findings from the Nun Study," Annals of Internal Medicine 139(5):450-454 (2003).
Sousa et al., "Interaction of the Receptor for Advanced Glycation End Products (RAGE) with Transthyretin Triggers Nuclear Transcription Factor kB (NF-kB) Activation," Laboratory Investigation 80(7):1101-1110 (2000).
Spite et al., "Novel Lipid Mediators Promote Resolution of Acute Inflammation: Impact of Aspirin and Statins," Circulation Research, 107:1170-1184 (2010).
Strittmatter et al., "Apolipoprotein E: High-avidity binding to beta-amyloid and increased frequency of type 4 allele in late-onset familial Alzheimer disease," Proc. Natl. Acad. Sci. USA 90:1977-1981 (1993).
T. Wendt et al., 185 Atherosclerosis 70-77 (2006).
Taguchi et al., "Blockade of RAGE-amphoterin signalling suppresses tumour growth and metastases," Nature 405:354-360 (2000).
Takuma et al., "RAGE-mediated signaling contributes to intraneuronal transport of amyloid-beta and neuronal dysfunction," PNAS 106(47):20021-20026 (2009).
Tanaka et al., "The Receptor for Advanced Glycation End Products in Induced by the Glycation Products Themselves . . . through SP-1 in Human Vascular Endothelial Cells," The Journal of Biological Chemistry 275(33):25781-25790 (2000).
Teillet et al., "Food Restriction Prevents Advanced Glycation End Product Accumulation and Retards Kidney Aging in Lean Rats," J. Am. Soc. Nephrol. 11:1488-1497 (2000).
Thompson, A. J. et al., "Protein Conformational Misfolding and Amyloid Formation: Characteristics of a New Class of Disorders that Include Alzheimer's and Prion Diseases," Current Medicinal Chemistry, 9:1751-1762 (2002).
Vellas, et al., ¿ Long-term changes in ADAS-cog: What is clinically relevant for disease modifying trails in Alzheimer?¿ (vol. 11, No. 4, 2007; Journal of Nutrition, Health & Aging).
Vlassara, "Advanced Glycation End-products and Atherosclerosis," Annals of Medicine 28:419-426 (1996).
Waller et al., "Status of the Coronary Arteries at Necropsy in Diabetes Mellitus with Onset After Age 30 Years: Analysis of 229 Diabetic Patients . . . Coronary Heart Disease and Comparison to 183 Control Subjects," The American Journal of Medicine 69:498-506 (1980).
Wang et al., "The Profile of Soluble Amyloid beta Protein in Cultured Cell Media: Detection and Quantification of Amyloid beta Protein and Variants by Immunoprecipitation-Mass Spectrometry," The Journal of Biological Chemistry 271(50):31894-31902 (1996).
Wautier et al., "Advanced glycation end products (AGEs) on the surface of diabetic erythrocytes bind to the vessel wall via a specific receptor inducing oxidant stress in the vasculature: A link between surface-associated AGEs and diabetic complications," Proc. Natl. Acad. Sci. USA 91:7742-7746 (1994).
Wautier et al., "Receptor-mediated Endothelial Cell Dysfunction in Diabetic Vasculopathy: Soluble Receptor for Advanced Glycation End Products Blocks Hyperpermeability in Diabetic Rats," J. Clin. Invest. 97(1):238-243 (1996).
Wisniewski et al., "Apolipoprotein E: a pathological chaperone protein in patients with cerebral and systemic amyloid," Neuroscience Letters 135:235-238 (1992).
Yan et al., "Amyloid-beta peptide-Receptor for Advanced Glycation Endproduct interaction elicits neuronal expression of macrophage-colony stimulating factor: A proinflammatory pathway in Alzheimer disease," Proc. Natl. Acad. Sci. USA 94:5296-5301 (1997).
Yan et al., "An intracellular protein that binds amyloid-beta peptide and mediates neurotoxicity in Alzheimer's disease," Nature 389:689-695 (1997).
Yan et al., "Enhanced Cellular Oxidant Stress by the Interaction of Advanced Glycation End Products with Their Receptors/Binding Proteins," The Journal of Biological Chemistry 269(13):9889-9897 (1994).
Yan et al., "RAGE and Alzheimer's Disease: A Progression Factor for Amyloid-beta-Induced Cellular Perturbation?" Journal of Alzheimer's Disease 16:833-843 (2009).
Yan et al., "RAGE and amyloid-beta peptide neurotoxicity in Alzheimer's disease," Nature 382:685-691 (1996).
Yan et al., "Receptor-dependent cell stress and amyloid accumulation in systemic amyloidosis," Nature Medicine 6(6):643-651 (2000).
Yankner el al., "Neurotrophic and Neurotoxic Effects of Amyloid beta Protein: Reversal by Tachykinin Neuropeptides," Science 250(4978):279-282 (1990).
Yeh et al., "Requirement for p38 and p44/p42 Mitogen-Activated Protein Kinases in RAGE-Mediated Nuclear Factor-kB Transcriptional Activation and Cytokine Secretion," Diabetes 50:1495-1504 (2001).
Zimmer et al., "The S100 Protein Family: History, Function, and Expression," Brain Research Bulletin 37(4):417-429 (1995).
Sabbagh MN et al., *Abstract* TTP488: From Futile to Fast Track. Presented at the 2015 Alzheimer's Association International Conference. Washington, DC, Jul. 2015 (1 page).
Sabbagh MN et al., TTP488: From Futility to Fast Track. Presented at the 2015 Alzheimer's Association International Conference. Washington, DC, Jul. 2015 (13 pages).
Sabbagh MN et al., *Abstract* TTP488 Path to Registration: Leveraging Enrichment Strategies. Presented at the 2015 Alzheimer's Association International Conference. Washington, DC, Jul. 2015 (1 page).

(56) References Cited

OTHER PUBLICATIONS

Sabbagh MN et al., TTP488 Path to Registration: Leveraging Enrichment Strategies. Presented at the 2015 Alzheimer's Association International Conference. Washington, DC, Jul. 2015 (1 page).
Burstein AH et al., *Abstract* Clinical support for advancement of the RAGE antagonist azeliragon into Phase 3 clinical investigation for mild Alzheimer's disease. Presented at the International Psychogeriatric Association International Congress. San Francisco, CA. Sep. 2016 (1 page).
Burstein AH et al., Clinical support for advancement of the RAGE antagonist azeliragon into Phase 3 clinical investigation for mild Alzheimer's disease. Presented at the International Psychogeriatric Association International Congress. San Francisco, CA. Sep. 2016 (13 pages).
Galasko, D., et al., "Clinical Trial of an Inhibitor of RAGE-Aβ Interactions in Alzheimer Disease," Neurology, 82, pp. 1536-1542 with supplemental content—25 pages in total (Apr. 29, 2014).

\* cited by examiner

TREATMENT OF MILD AND MODERATE ALZHEIMER'S DISEASE

FIELD OF THE INVENTION

The present invention relates to a method of treating individuals suffering from mild-to-moderate dementia of Alzheimer's type by administering an effective amount of [3-(4-{2-butyl-1-[4-(4-chloro-phenoxy)-phenyl]-1H-imidazol-4-yl}-phenoxy)-propyl]-diethyl amine ("COMPOUND I"). The present invention also relates to a method of inhibiting the interaction of the receptor for advanced glycation end products (RAGE) with a RAGE ligand in individuals with mild-to-moderate Alzheimer's disease. The present invention also relates to a method for treating diabetes and the reduction of glucose metabolism, including in individuals suffering from mild-to-moderate Alzheimer's disease. Additionally, the present invention relates to a method for treating insomnia or sleep onset latency in individuals, including those suffering from mild-to-moderate Alzheimer's disease.

BACKGROUND OF THE INVENTION

RAGE and the Treatment of Disease

The Receptor for Advanced Glycation Endproducts (RAGE) is a member of the immunoglobulin super family of cell surface molecules. The extracellular (N-terminal) domain of RAGE includes three immunoglobulin-type regions, one V (variable) type domain followed by two C-type (constant) domains (Neeper et al., J. Biol. Chem. 267:14998-15004 (1992)). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hori et al. (1995)). Increased levels of RAGE are also found in aging tissues (Schleicher et al., J. Clin. Invest. 99 (3): 457-468 (1997)), and the diabetic retina, vasculature and kidney (Schmidt et al., Nature Med. 1:1002-1004 (1995)). Activation of RAGE in different tissues and organs leads to a number of pathophysiological consequences. RAGE has been implicated in a variety of conditions including: acute and chronic inflammation (Hofmann et al., Cell 97:889-901 (1999)), the development of diabetic late complications such as increased vascular permeability (Wautier et al., J. Clin. Invest. 97:238-243 (1996)), nephropathy (Teillet et al., J. Am. Soc. Nephrol. 11:1488-1497 (2000)), atherosclerosis (Vlassara et. al., The Finnish Medical Society DUODECIM, Ann. Med. 28:419-426 (1996)), and retinopathy (Hammes et al, Diabetologia 42:603-607 (1999)). RAGE has also been implicated in Alzheimer's disease (Yan et al. Nature 382: 685-691 (1996)), erectile dysfunction, and in tumor invasion and metastasis (Taguchi et al. Nature 405: 354-357 (2000)).

Advanced glycation endproducts (AGEs) have been implicated in a variety of disorders including complications associated with diabetes and normal aging. Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as AGEs. Factors which promote formation of AGEs include delayed protein turnover (e.g. as in amyloidoses), accumulation of macromolecules having high lysine content, and high blood glucose levels (e.g. as in diabetes) (Hori et al, J. Biol. Chem. 270: 25752-761, (1995)).

AGEs display specific and saturable binding to cell surface receptors on endothelial cells of the microvasculature, monocytes and macrophages, smooth muscle cells, mesengial cells, and neurons.

In addition to AGEs, other compounds can bind to, and inhibit the interaction of physiological ligands with RAGE. In normal development, RAGE interacts with amphoterin, a polypeptide which mediates neurite outgrowth in cultured embryonic neurons (Hori et al, (1995)). RAGE has also been shown to interact with EN-RAGE, a protein having substantial similarity to calgranulin (Hofmann et al. (1999)). RAGE has also been shown to interact with β-amyloid (Yan et al. Nature 389:689-695 (1997); Yan et al. Nature 382:685-691 (1996); Yan et al, Proc. Natl. Acad. Sci, 94:5296-5301 (1997)).

Binding of ligands such as AGEs, S100/calgranulin/EN-RAGE, β-amyloid, CML (Ne-Carboxymethyl lysine), HMGB1 (high mobility group box 1) and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-I β, TNF-a, and the like.

As noted above, RAGE antagonists are useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D, et al., J. Clin. Invest., 91:2463-2469 (1993); Reddy, S., et al., Biochem., 34:10872-10878 (1995); Dyer, D., et al., J. Biol. Chem., 266: 11654-1 1660 (1991); Degenhardt, T., et al., Cell Mol. Biol, 44: 1139-1 145 (1998)). Accumulation of AGEs in the vasculature can occur focally, as in the joint amyloid composed of AGE-B2-microglobulin found in patients with dialysis-related amyloidosis (Miyata, T, et al, J. Clin. Invest, 92: 1243-1252 (1993); Miyata, T, et al, J. Clin. Invest, 98:1088-1094 (1996)), or generally, as exemplified by the vasculature and tissues of patients with diabetes (Schmidt, A-M, et al. Nature Med, 1:1002-1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., J. Biol. Chem., 272: 16498-16506 (1997); Li, J., et al., J. Biol. Chem., 273:30870-30878 (1998); Tanaka, N., et al., J. Biol. Chem., 275:25781-25790 (2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

RAGE antagonists are also useful in treating amyloidoses and/or Alzheimer's disease. RAGE appears to be a cell surface receptor which binds β-sheet fibrillar material regardless of the composition of the subunits (amyloid-β peptide, Aβ, amylin, serum amyloid A, prion-derived peptide) (Yan, S.-D., et al., Nature, 382:685-691 (1996); Yan, S-D, et al, Nat. Med, 6:643-651 (2000)). Deposition of amyloid has been shown to result in enhanced expression of RAGE. For example, in the brains of patients with Alzheimer's disease, RAGE expression increases in neurons and glia (Yan, S.-D, et al. Nature 382:685-691 (1996)). The consequences of Aβ interaction with RAGE appear to be quite different on neurons versus microglia. Whereas microglia become activated as a consequence of Aβ-RAGE interaction, as reflected by increased motility and expression of cytokines, early RAGE-mediated neuronal activation is superceded by cytotoxicity at later times. Further evidence of a role for RAGE in cellular interactions of Aβ concerns inhibition of Aβ-induced cerebral vasoconstriction and transfer of the peptide across the blood-brain barrier to brain parenchyma when the receptor was blocked (Kumar, S, et al, Neurosci. Program, p141 (2000)). Inhibition of RAGE-amyloid interaction has been shown to decrease expression of cellular RAGE and cell stress markers (as well as NF-kB activation), and diminish amyloid deposition (Yan, S-D, et al, Nat. Med, 6:643-651 (2000)) suggesting a role for RAGE-amyloid interaction in both perturbation of cellular properties in an environment enriched for amyloid (even at early stages) as well as in amyloid accumulation.

SUMMARY OF THE INVENTION

The present invention provides a method for the treatment of mild-to-moderate Alzheimer's disease by administering to a subject in need thereof an effective amount of [3-(4-{2-butyl-1-[4-(4-chloro-phenoxy)-phenyl]-1H-imidazol-4-yl}-phenoxy)-propyl]-diethyl amine ("COMPOUND I") or a pharmaceutically acceptable salt thereof.

In one embodiment, COMPOUND I or a pharmaceutically acceptable salt thereof is administered in an amount of less than 20 mg per day.

In another embodiment, COMPOUND I or a pharmaceutically acceptable salt thereof is administered between 1 mg/5 kg of the subject's body weight per day to 1 mg/50 kg of the subject's body weight per day.

In yet another embodiment, the present invention provides a method for inhibiting the interaction of the receptor for advanced glycation end products (RAGE) with a RAGE ligand in subjects with mild-to-moderate Alzheimer's disease, comprising administering to a subject in need thereof an amount less than 20 mg per day of COMPOUND I or a pharmaceutically acceptable salt thereof.

In a further embodiment, the present invention provides a method of treating diabetes comprising administering to a subject in need thereof an amount less than 20 mg per day of COMPOUND I or a pharmaceutically acceptable salt thereof.

The present invention also provides a method for inhibiting the reduction of glucose metabolism associated with the regression of subjects with mild-to-moderate Alzheimer's disease, comprising administering to a subject in need thereof an amount less than 20 mg per day of COMPOUND I or a pharmaceutically acceptable salt thereof.

In another embodiment, the present invention provides a method of lowering blood glucose levels in a subject comprising administering to a subject in need thereof an amount less than 20 mg per day of COMPOUND I or a pharmaceutically acceptable salt thereof.

In yet another embodiment, the present invention also provides of treating insomnia comprising administering to a subject in need thereof an amount less than 20 mg per day of COMPOUND I or a pharmaceutically acceptable salt thereof.

In another embodiment, the treatment of insomnia is in a subject with mild-to-moderate Alzheimer's disease.

The present invention also provides a method of decreasing sleep onset latency comprising administering to a subject in need thereof an amount less than 20 mg per day of COMPOUND I or a pharmaceutically acceptable salt thereof.

In yet another embodiment, the method of decreasing sleep onset latency is in a subject with mild-to-moderate Alzheimer's disease.

In another embodiment, the present invention provides a method of reducing the frequency of adverse events in a subject with mild-to-moderate Alzheimer's disease comprising administering to a subject in need thereof an amount less than 20 mg per day of COMPOUND I or a pharmaceutically acceptable salt thereof.

In another embodiment of any of the previous embodiments, a suitable amount of an acetylcholinesterase inhibitor (AChEI) or memantine may also be administered.

The present invention also provides a pharmaceutical composition comprising between 1 mg and 20 mg of COMPOUND I or a pharmaceutically acceptable salt thereof.

In another embodiment, the pharmaceutical composition includes an acetylcholinesterase inhibitor (AChEI).

In still another embodiment, the pharmaceutical composition includes memantine.

DETAILED DESCRIPTION

Figure 1:
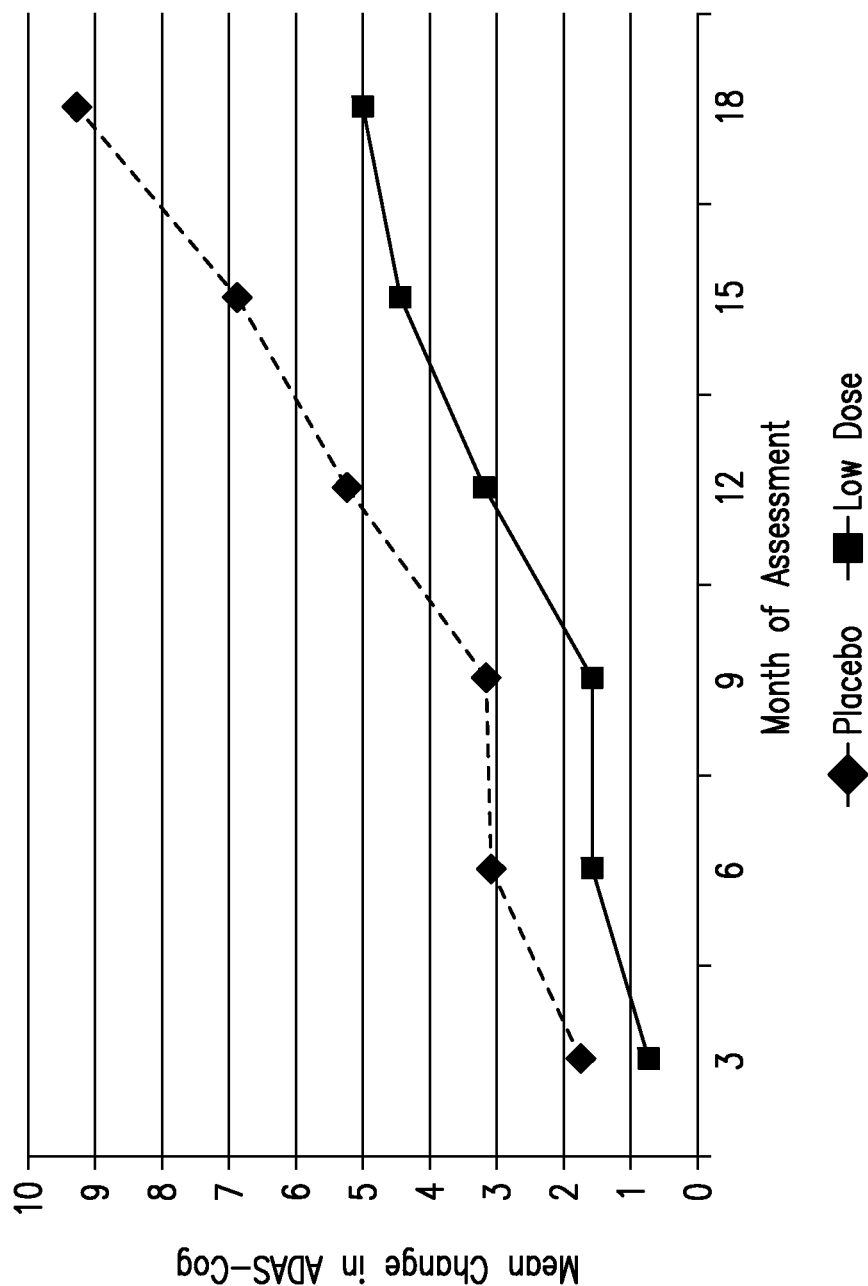
FIG. 1—Graph displaying the change from baseline in ADAS-cog for ADAS-cog subgroup of subjects presenting with ADAS-cog scores at baseline of less than or equal to 22.8 between placebo and treatment with 5 mg of COMPOUND I.

The present invention demonstrates that subjects with mild-to-moderate Alzheimer's disease may benefit from dose-dependent treatment with COMPOUND I compared with placebo. Further, the present invention demonstrates that treatment with COMPOUND I may lower glucose levels and may inhibit reduction in glucose metabolism that is associated with the regression of subjects with mild-to-moderate Alzheimer's disease. Additionally, the present invention provides a treatment for insomnia or sleep onset latency in subjects, including those with mild-to-moderate Alzheimer's disease by providing subjects with an effective amount of COMPOUND I or a pharmaceutically acceptable salt thereof.

The present invention is based on results from a parallel three-arm phase 2 study to evaluate the safety, tolerability, and efficacy of two doses of COMPOUND I compared to placebo in subjects with mild-to-moderate Alzheimer's disease. The study was conducted at forty different study sites across the United States.

In the study of the present invention, there were 399 subjects (133 per group), who were randomized to placebo or to COMPOUND I administered at 20 mg daily (after a loading dose of 60 mg daily for 6 days), or to COMPOUND I administered at 5 mg daily (after a loading dose of 15 mg daily for 6 days).

Study visits occurred at screening, baseline (within four weeks after screening), then at four weeks, 3, 6, 9, 12, 15, 18 months, with a safety follow-up visit at 21 months. Visits included clinical and safety evaluations, blood draw for plasma biomarker and pharmacokinetic analysis, and pill counts to assess compliance. Primary (clinical) outcome measures were obtained at baseline and at subsequent three monthly visits, and secondary clinical outcome measures at baseline and at six monthly intervals. Brain MRIs were obtained at baseline, 12 and 18 months. Lumbar punctures for CSF biomarkers were performed at baseline and 12 months on a subgroup of subjects.

Key eligibility criteria included subjects who were aged 50 or older; had a diagnosis of probable Alzheimer's disease; had a Mini-Mental State Examination (MMSE) score between 14 and 26; and were in good general health. Subjects could have no evidence of stroke contributing to dementia. Further inclusion criteria included treatment with a stable dose of an acetylcholinesterase inhibitor and/or memantine for at least four months prior to randomization, and an available caregiver to act as informant and supervise study medications. Exclusion criteria included uncontrolled hypertension, unstable cardiac or pulmonary disease, diabetes, weight less than 40 kg or greater than 100 kg within the past two years, chronic use of non-steroidal anti-inflammatory drugs or immunosuppressive agents, drugs that increase QTc or inhibit CYP 34A, markedly abnormal ECG or QTc (QTcB or QTcF) or any screening 12-lead ECG greater than 450 msec for females or greater than 430 msec for males. There also could be no history of treatment for cancer within the past five years, drug or alcohol abuse, or major psychiatric illness. Women could not be of child-bearing potential. Subjects could not have taken another investigational drug for three months before screening.

The primary efficacy measure was the 70-point ADAS-cog. The ADAS-cog is used to assess the severity of selected areas of cognitive impairment (memory, language, orientation, reason and praxis). Scores range from 0 to 70 with lower scores indicating lesser severity and a score of 70 representing the worst cognitive impairment. Its use in assessing and following changes in patients with mild to moderate Alzheimer's disease has been extensively validated. Primary safety measures included reports of adverse events, blood and urine tests, and ECG measures. Secondary clinical measures included Clinical Dementia Rating Sum of Boxes (CDR-sb); Alzheimer's Disease Cooperative Study Activities of Daily Living Scale (ADCS-ADL); Neuropsychiatric Inventory (NPI); and MMSE. Subjects also received a neuropsychological test battery, including: Digit Symbol Substitution Test, Forward and Backward Digit Span Test, Controlled Oral Word Association Test, Stroop Color Word interference Test, and Trail-Making Test (Parts A and B). Caregivers received a Quality of Life questionnaire and a Resource Utilization Schedule.

A brain MRI was performed at baseline and 12 months, on 1.5 T scanners, using standardized acquisition parameters based on those in the ADNI study, and used for volumetric analysis. Cerebrospinal fluid was obtained by lumbar puncture, at baseline and after 12 months, for analysis of Alzheimer's disease-related biomarkers. Apolipoprotein E (APO-E) genotyping was performed and DNA was banked for pharmacogenomic studies on subjects who consented. Plasma was assayed for study drug levels at each visit and was stored for biomarker studies. Further, complete physical and neurological examinations were performed at baseline, and vital signs and brief examinations at subsequent visits. Clinical laboratory studies and urinalysis were performed at every visit. Electrocardiograms (ECGs) were obtained at all visits and centrally read (QTc analysis by a cardiologist). Adverse events were classified according to severity and causality by site investigators and reported to the ADCS and sponsors using standard methods. If subjects decided to withdraw from the study or were discontinued by site investigators, an early termination visit was scheduled within 14 days, including clinical and safety evaluations similar to the baseline visit.

Definitions

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

By percent by weight it is meant that a particular weight of one ingredient in a composition is divided by the total weight of all of the ingredients in that composition. Percent by weight may be used interchangeably and means approximately the same as weight/weight percent or % (weight/weight) or percent by mass or mass percent.

It is further noted that, as used in this specification, the singular forms "a," "an," and "the" include plural referents unless expressly and unequivocally limited to one referent.

In another embodiment, the dosage or blood level of COMPOUND I or a pharmaceutically acceptable salt thereof and administration may be sufficient for inhibition of the biological function of RAGE at a sufficient level for sufficient time to treat Alzheimer's disease.

COMPOUND I refers to [3-(4-{2-butyl-1-[4-(4-chloro-phenoxy)-phenyl]-1H-imidazol-4-yl}-phenoxy)-propyl]-diethyl amine. COMPOUND I is the subject matter of U.S. Pat. Nos. 7,361,678 and 7,884,219.

Various salts and isomers of COMPOUND I can be used. The term "salts" can include acid addition salts or addition salts of free bases. Examples of acids which may be employed to form pharmaceutically acceptable acid addition salts include inorganic acids such as hydrochloric, sulfuric, or phosphoric acid, and organic acids such as acetic, maleic, succinic, or citric acid, etc. All of these salts (or other similar salts) may be prepared by conventional means. The nature of the salt is not critical, provided that it is non-toxic and does not substantially interfere with the desired pharmacological activity. A preferred salt for the method of the present invention is the hydrochloride salt.

The phrase "pharmaceutically acceptable", as used in connection with compositions of the invention, refers to molecular entities and other ingredients of such compositions that are physiologically tolerable and do not typically produce untoward reactions (toxicity or side effects) when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. Berge, et al. Journal of Pharmaceutical Science, Vol. 66(1), pp. 1-19 (1977).

The term "carrier" applied to pharmaceutical compositions of the invention refers to a diluent, excipient, or vehicle with which an active compound (e.g., an 1-aminocyclohexane derivative) is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18$^{th}$ Edition.

The term "subject" or "subject in need thereof" as used herein refers to a mammal. In an embodiment, the term refers to humans diagnosed with mild-to-moderate Alzheimer's disease.

"Mild-to-moderate Alzheimer's disease" can be diagnostically assessed as "probable Alzheimer's" according to the National Institute of Neurological and Communicative Disorders and Stroke/the Alzheimer's Disease and Related Disorders Associations (NINCDS-ADRDA) criteria.

The diagnosis of "mild-to-moderate" is well within the purview of the ordinary skilled physician using standard criteria, including the clinical assessment scales disclosed above and below. By way of example, the following numerical ranges on the standardized Mini-Mental State Examination (MMSE; 0-30 scale) have been used to diagnose mild-to-moderate, moderate, and moderate-to-severe Alzheimer's.

Mild-to-moderate Alzheimer's disease has been diagnosed as determined by MMSE scores of 10 to 22 in the present study, and also from 10-26 in studies using other therapeutics for treating mild-to-moderate Alzheimer's (e.g., donepezil). Severe Alzheimer's has been diagnosed in subjects having MMSE scores of less than 10.

Accordingly, a diagnosis of "mild" Alzheimer's disease could be made for subjects having the higher scores within the above-described ranges, e.g., about 21 to 26 on the MMSE.

It should be noted that the MMSE scale is not the only way to diagnose mild Alzheimer's disease, but represents a convenience. Nor should the claims be construed as requiring the step of "grading" a subject on the MMSE scale to be performed. In an embodiment, a subject having mild Alzheimer's disease is a patient who would score 21 or higher if the patient were scored according to MMSE scale. If a different scale were to be used, "mild" Alzheimer's disease would be defined as a diagnosis of Alzheimer's disease or probable Alzheimer's disease which is made based on a score that clearly does not overlap with the score range for moderate-to-severe Alzheimer's disease established for the same scale.

In an embodiment, mild Alzheimer's disease is defined as individuals having an ADAS-cog score of less than or equal to 23.

The term "intent to treat principle" refers to the principle that asserts that the effect of a treatment policy can be best assessed by evaluating on the basis of the intention to treat a subject (i.e. the planned treatment regimen) rather than the actual treatment given. It has the consequence that subjects allocated to a treatment group should be followed up, assessed and analyzed as members of that group irrespective of their compliance to the planned course of treatment. It is noted that the ITT principle refers to a methodology (how), not a population of analysis (who). It is also noted that the ITT analyses are generally accepted as the most valid analyses in that they are supported by randomization, and exclusion of a subject based on behavior characteristics of the subject (e.g., compliance with trial medication) is not consistent with the ITT principle because it is not supported by randomization. It is also noted that subgroup analyses based on population characteristics (e.g., severity of AD at baseline) are supported by randomization and considered valid.

The term "Full Analysis Set (FAS)" refers to the set of subjects that is as close as possible to the ideal implied by the intention-to-treat principle. It is derived from the set of all randomized subjects by minimal and justified elimination of subjects. The FAS includes all subjects who receive at least one dose of trial medication and have at least one post-baseline assessment. The dataset for the FAS includes all collected data whether on treatment or off-treatment (it is irrelevant to treatment compliance). It is noted that observations of subjects after treatment has discontinued are still included in a pure ITT analysis recognizing that the treatment that was received, particularly with a compound with a long half-life, affects assessments collected after treatment, regardless of whether or not the subject is still taking active treatment.

The term "on treatment" refers to data collected within 28 days of last dose. All data collected between the first dose of trial medication and the last dose of trial medication and all data collected within 28 days of the last dose of trial medication are considered to be on-treatment."

The term "off treatment" refers to data collection 29 days or later following the final dose of trial medication.

The term "trial medication" refers to all blinded medication within a clinical trial whether active or placebo.

The term "post baseline" refers to all data collected after baseline regardless of whether it is on treatment or off treatment.

The term "Per Protocol Set (Valid Cases, Efficacy Sample, Evaluable Subjects Sample)" or "per-treatment set" refers to the set of data generated by the subset of subjects who complied with the protocol sufficiently to ensure that these data would be likely to exhibit the effects of treatment, according to the underlying scientific model. Compliance covers such considerations as exposure to treatment, availability of measurements and absence of major protocol violations. It is noted that a per-treatment analysis excludes subjects based on behavior characteristics and is not generally supported by randomization. Such analyses can be useful, but are not generally as valid as ITT analyses.

The term "Statistical Analysis Plan (SAP)" refers to a document that contains the analyses planned in advance of unblinding to protect alpha. It is a more technical and detailed elaboration of the principal features of the analysis described in the protocol, and includes detailed procedures for executing the statistical analysis of the primary and secondary variables and other data. The SAP is generally signed prior to unblinding, and modifications to the SAP after unblinding, such as unplanned analyses based on post-hoc behavior of a subject (e.g., treatment compliance).

The term "dropout" refers to a subject in a clinical trial who for any reason fails to continue in the trial until the last visit required of him/her by the study protocol. In particular, in these studies, a subject is a dropout when the subject's last visit occurred prior to Month 18.

The term "Treatment Effect" refers an effect attributed to a treatment in a clinical trial. In most clinical trials the treatment effect of interest is a comparison (or contrast) of two or more treatments. It is noted that the treatment effect does not include the placebo effect. Differences between randomized active treatment groups and placebo groups are generally recognized as treatment effects in controlled clinical trials.

The term "treatment-emergent" refers to an observation or event that emerges during treatment having been absent pre-treatment, or worsens relative to the pre-treatment state.

The term "treatment-emergent adverse event" refers to any untoward event that is observed or reported after the first dose of trial medication that was not present prior to the first dose of trial medication or any untoward event that represents the exacerbation of a pre-existing condition. Exacerbation includes any increase in severity or frequency.

The term "Generalisability, Generalisation" refers to the extent to which the findings of a clinical trial can be reliably extrapolated from the subjects who participated in the trial to a broader patient population and a broader range of clinical settings.

The term "treatment" as used herein, refers to the full spectrum of treatments for a given condition or disorder from which a subject is suffering, including alleviation or amelioration of one or more of the symptoms resulting from that disorder, to the delaying of the onset or progression of the disorder.

The term "treat" is used herein to mean to relieve or alleviate at least one symptom of a disease in a subject. For example, the term "treat" may mean to relieve or alleviate cognitive impairment (such as impairment of memory and/or orientation) or impairment of global functioning (activities of daily living) and/or slow down or reverse the progressive deterioration in ADL or cognitive impairment in individuals having mild-to-moderate Alzheimer's disease.

Within the meaning of the present invention, the term "treat" may also mean delay of the progression of a disease in the patients presenting with additional symptoms associated with Alzheimer's disease, such as but not limited to those identified using one or more of the ADAS-cog, the MMSE, the ADCS-ADL criteria, the CDR-sb, or the NPI total criteria, defined above. The term "delay the progression" is used herein to mean slower than expected development or continuance or aggravation of a disease in a subject compared to an untreated subject. This can be determined for Alzheimer's disease, for example, by obtaining slower than expected deterioration in measures such as cognitive performance in treated patients, compared with those measures in untreated patients (who represent the expected progression of the disease). Cognitive performance can be measured using, e.g., the Alzheimer's Disease Assessment Scale (ADAS-cog), or the Alzheimer's Disease Cooperative Study-Activities of Daily Living (ADCS-ADL). For example, the typical disease progression in subjects with mild Alzheimer's disease is an increase of about 1 to about 3 points on the ADAS-cog over a time period of about 6 months. However, disease progression is highly individualized, and also depends on factors such as the initial condition of the patient.

In a specific embodiment, the term "treat" may also mean to increase the glucose metabolic rate, or to inhibit further reduction in the metabolic rate in patients with mild-to-moderate Alzheimer's disease, which is associated with regression. This can also be assessed by comparing the glucose metabolism in treated patients with that in untreated patients. A reduction in the decrease of glucose metabolism in the treated patients, or a slower than expected decrease, or stability of glucose metabolism in treated patients, compared with untreated patients, is indicative of a benefit accompanying the treatment.

In another specific embodiment, the term "treat" may also mean to improve symptoms associated with insomnia or decrease sleep onset latency in patients with mild-to-moderate Alzheimer's disease, which is associated with regression.

The term "therapeutically effective amount" is used herein to mean an amount or dose of COMPOUND I that is effective to ameliorate or delay a symptom, behavior or event associated with mild-to-moderate Alzheimer's disease. Alternatively, a therapeutically effective amount is sufficient to cause an improvement in a clinically significant condition or parameter (according to the attending physician employing one or more of the foregoing sets of criteria) associated with Alzheimer's disease in an individual in need thereof. In still another embodiment, a therapeutically effective amount is used herein to denote the amount of COMPOUND I or a pharmaceutically acceptable salt thereof that will elicit the therapeutic response of a subject that is being sought. In an embodiment, the therapeutic response may be antagonizing RAGE.

A "responder" is defined as a patient who has not progressed and for whom the change from baseline to 18 months in ADAS-cog is less than or equal to 7.

The terms "about" and "approximately" shall generally mean an acceptable degree of error or variation for the quantity measured given the nature or precision of the measurements. Typically, degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

Formulation, Dosage, and Administration

The invention further provides pharmaceutical compositions comprising a compound of COMPOUND I or a pharmaceutically acceptable salt thereof and a pharmaceutically acceptable carrier. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intraci sternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, lotions, eye ointments and eye or ear drops, impregnated dressings and aerosols etc., containing the compounds of the invention are contemplated. These topical formulations may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 0.1% up to about 99% of the formulation. More usually they will form up to about 80% of the formulation. For the purpose of this application, topical applications shall include mouth washes and gargles.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas.

In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The equipment and parameters listed in the following manufacturing description are representative of the equipment and parameters that may be used to prepare a pharmaceutical formulation. The actual equipment and parameters used in the manufacture of a pharmaceutical formulation may vary.

The compound (in free base form) may be sifted and weighed out with an approximately equal amount of microcrystalline cellulose. The mixture may be geometrically diluted with microcrystalline cellulose. The mixture, any remaining microcrystalline cellulose, lactose monohydrate, croscarmellose sodium, colloidal silicon dioxide, and Starch 1500 may be added into a blender and mixed. A small portion of the mixture may be removed, combined with magnesium stearate, and returned to the blender and mixed. The resulting mixed may be encapsulated and administered. The weight percent of the compound, microcrystalline cellulose, and/or lactose monohydrate may be adjusted to prepare dosages with higher or lower amounts of the compound. For example, Formulation A in the table below may be used to prepare a capsule formulation of 5 mg per dose, and Formula B may be used to prepare a capsule formulation of 20 mg per dose.

| Name of Ingredients | Formulation A (wt %) | Formulation B (wt %) |
| --- | --- | --- |
| Compound (free base) | 2.4 | 9.5 |
| Microcrystalline Cellulose | 54.2 | 50.6 |
| Lactose Monohydrate | 27.9 | 24.4 |
| Pregelatinized Starch | 8.0 | 8.0 |
| Croscarmellose Sodium | 6.4 | 6.4 |
| Colloidal Silicon Dioxide | 0.4 | 0.4 |
| Magnesium Sterarate | 0.8 | 0.8 |

In one embodiment, a method of treating Alzheimer's disease comprises administering to a subject in need thereof an amount less than 20 mg per day of COMPOUND I or a pharmaceutically acceptable salt thereof. COMPOUND I or a pharmaceutically acceptable salt thereof may be administered in a dose ranging from about 1 mg per day to less than 20 mg per day. In some embodiments, the dose is from about 1 mg per day to about 19 mg per day, or from about 1 mg per day to about 18 mg per day, or from about 1 mg per day to about 17 mg per day, or from about 1 mg per day to about 16 mg per day, or from about 1 mg per day to about 15 mg per day, or from about 1 mg per day to about 14 mg per day, or from about 1 mg per day to about 13 mg per day, or from about 1 mg per day to about 12 mg per day, or from about 1 mg per day to about 11 mg per day, or from about 1 mg per day to about 10 mg per day, or from about 1 mg per day to about 9 mg per day, or from about 1 mg per day to about 8 mg per day, or from about 1 mg per day to about 7 mg per day, or from about 1 mg per day to about 6 mg per day, or from about 1 mg per day to about 5 mg per day, or from about 1 mg per day to about 4 mg per day, or from about 1 mg per day to about 3 mg per day, or from about 1 mg per day to about 2 mg per day. In other embodiments, the dose is about 5 mg per day or about 4 mg per day or about 3 mg per day or about 2 mg per day.

In some embodiments, the serum blood concentration of COMPOUND I or a pharmaceutically acceptable salt thereof in a subject is between about 1 ng/ml to about 65 ng/ml, or between about 1 ng/ml to about 60 ng/ml, or between about 1 ng/ml to about 55 ng/ml, or between about 1 ng/ml to about 50 ng/ml, or between about 1 ng/ml to about 45 ng/ml, or between about 1 ng/ml to about 40 ng/ml, or between about 1 ng/ml to about 35 ng/ml, or between about 1 ng/ml to about 30 ng/ml, or between about 1 ng/ml to about 25 ng/ml, or between about 1 ng/ml to about 20 ng/ml, or between about 1 ng/ml to about 15 ng/ml, or between about 1 ng/ml to about 10 ng/ml. In other embodiments, the serum blood concentration in the subject is between 8 to about 15 ng/ml. In still other embodiments, the serum blood concentration in the subject is about 12.5 ng/ml.

In another embodiment, the method of the treatment of Alzheimer's disease is determined by the improvement, or no deterioration, or a reduction in the rate of deterioration in at least one of the assessments selected from the group consisting of Alzheimer's Disease Assessment Scale-cognitive subscale (ADAS-cog), the Clinical Dementia Rating Sum of Boxes (CDR-sb), the Alzheimer's Disease Cooperative Study Activities of Daily Living Scale (ADCS-ADL), the Neuropsychiatric Inventory (NPI), and the Mini-Mental State Evaluation (MMSE). In some embodiments, the treatment results in a reduction in the rate of deterioration in ADAS-cog scores. In other embodiments, the treatment results in a median reduction in the rate of deterioration of ADAS-cog scores of two to five points.

In other embodiments, a method of treating Alzheimer's disease comprises administering to a subject in need thereof an amount of COMPOUND I or a pharmaceutically acceptable salt thereof between 1 mg/5 kg of the subject's body weight per day and 1 mg/50 kg of the subject's body weight per day. The administration of COMPOUND I or a pharmaceutically acceptable salt thereof may be administered in an amount of about 1 mg/10 kg per day, or 1 mg/15 kg per day, or 1 mg/20 kg per day, or 1 mg/25 kg per day, or 1 mg/30 kg per day, or 1 mg/35 kg per day, or 1 mg/40 kg per day, or 1 mg/45 kg per day. In yet other embodiments, COMPOUND I or a pharmaceutically acceptable salt thereof is administered in an amount of 1 mg/20 kg per day. In yet other embodiments, COMPOUND I or a pharmaceutically acceptable salt thereof is administered in an amount between about 0.2 mg/kg per day and 0.02 mg/kg per day.

In yet other embodiments, COMPOUND I or a pharmaceutically acceptable salt thereof is administered in an amount between about 0.1 mg/kg per day, or about 0.09 mg/kg per day, or about 0.08 mg/kg per day, or about 0.07 mg/kg per day, or about 0.06 mg/kg per day, or about 0.05 mg/kg per day, or about 0.04 mg/kg per day, or about 0.03 mg/kg per day.

In some embodiments, a method is provided to inhibit the interaction of the receptor for advanced glycation end products (RAGE) with a RAGE ligand in subjects with mild-to-moderate Alzheimer's disease, by administering to a subject in need thereof an amount less than 20 mg per day of COMPOUND I or a pharmaceutically acceptable salt thereof. In an embodiment, the RAGE ligand may be one of soluble β-amyloid, insoluble β-amyloid, s100b, calgranulin, EN-RAGE, HMGB1 (high mobility group box 1), aphoterin, or carboxymethyllysine. COMPOUND I or a pharmaceutically acceptable salt thereof may be administered in a dose ranging from about 1 mg per day to less than 20 mg per day. In some embodiments, the dose is from about 1 mg per day to about 19 mg per day, or from about 1 mg per day to about 18 mg per day, or from about 1 mg per day to about 17 mg per day, or from about 1 mg per day to about 16 mg per day, or from about 1 mg per day to about 15 mg per day, or from about 1 mg per day to about 14 mg per day, or from about 1 mg per day to about 13 mg per day, or from about 1 mg per day to about 12 mg per day, or from about 1 mg per day to about 11 mg per day, or from about 1 mg per day to about 10 mg per day, or from about 1 mg per day to about 9 mg per day, or from about 1 mg per day to about 8 mg per day, or from about 1 mg per day to about 7 mg per day, or from about 1 mg per day to about 6 mg per day, or from about 1 mg per day to about 5 mg per day, or from about 1 mg per day to about 4 mg per day, or from about 1 mg per day to about 3 mg per day, or from about 1 mg per day to about 2 mg per day. In other embodiments, the dose is about 5 mg per day or about 4 mg per day or about 3 mg per day or about 2 mg per day.

In an embodiment, the administration of COMPOUND I or a pharmaceutically acceptable salt thereof treats mild Alzheimer's disease. In some embodiments, mild Alzheimer's disease may be defined as a subject that presents with an ADAS-cog score of less than or equal to 23.

In other embodiments, treatment with COMPOUND I or a pharmaceutically acceptable salt thereof is used to treat diabetes by administering to a subject in need thereof an amount less than 20 mg per day. In other embodiments, COMPOUND I or a pharmaceutically acceptable salt thereof is administered in a dose from about 1 to about 20 mg per day. COMPOUND I or a pharmaceutically acceptable salt thereof may be administered in a dose ranging from about 1 mg per day to less than 20 mg per day. In some embodiments, the dose is from about 1 mg per day to about 19 mg per day, or from about 1 mg per day to about 18 mg per day, or from about 1 mg per day to about 17 mg per day, or from about 1 mg per day to about 16 mg per day, or from about 1 mg per day to about 15 mg per day, or from about 1 mg per day to about 14 mg per day, or from about 1 mg per day to about 13 mg per day, or from about 1 mg per day to about 12 mg per day, or from about 1 mg per day to about 11 mg per day, or from about 1 mg per day to about 10 mg per day, or from about 1 mg per day to about 9 mg per day, or from about 1 mg per day to about 8 mg per day, or from about 1 mg per day to about 7 mg per day, or from about 1 mg per day to about 6 mg per day, or from about 1 mg per day to about 5 mg per day, or from about 1 mg per day to about 4 mg per day, or from about 1 mg per day to about 3 mg per day, or from about 1 mg per day to about 2 mg per day. In other embodiments, the dose is about 5 mg per day or about 4 mg per day or about 3 mg per day or about 2 mg per day. In still other embodiments, the method includes treating diabetes in patients with mild-to-moderate Alzheimer's disease.

In some embodiments, the administration of COMPOUND I or a pharmaceutically acceptable salt thereof may reduce the levels of HbA1C in a subject in need thereof. In other embodiments, the administration of COMPOUND I or a pharmaceutically acceptable salt thereof may reduce the amount of HbA1C in a subject in need thereof by at least 0.1 of a percentage point, or 0.2 of a percentage point, or 0.3 of a percentage point, or 0.4 of a percentage point, or 0.5 of a percentage point, or 0.6 of a percentage point, or 0.7 of a percentage point, or 0.8 of a percentage point, or 0.9 of a percentage point, or one percentage point. In still other embodiments, the administration of COMPOUND I or a pharmaceutically acceptable salt thereof may reduce the level of HbA1C in a subject in need thereof to less than 7%. In other embodiments, the level of HbA1C may be reduced to a level between 5 and 6.5%.

In some embodiments, the present invention provides a method for inhibiting the reduction of glucose metabolism associated with the regression of subjects with mild-to-moderate Alzheimer's disease by administering to a subject in need thereof an amount less than 20 mg per day of COMPOUND I or a pharmaceutically acceptable salt thereof. COMPOUND I may be administered in a dose ranging from about 1 mg per day to less than 20 mg per day. In some embodiments, the dose is from about 1 mg per day to about 19 mg per day, or from about 1 mg per day to about 18 mg per day, or from about 1 mg per day to about 17 mg per day, or from about 1 mg per day to about 16 mg per day, or from about 1 mg per day to about 15 mg per day, or from about 1 mg per day to about 14 mg per day, or from about 1 mg per day to about 13 mg per day, or from about 1 mg per day to about 12 mg per day, or from about 1 mg per day to about 11 mg per day, or from about 1 mg per day to about 10 mg per day, or from about 1 mg per day to about 9 mg per day, or from about 1 mg per day to about 8 mg per day, or from about 1 mg per day to about 7 mg per day, or from about 1 mg per day to about 6 mg per day, or from about 1 mg per day to about 5 mg per day, or from about 1 mg per day to about 4 mg per day, or from about 1 mg per day to about 3 mg per day, or from about 1 mg per day to about 2 mg per day.

In other embodiments, the dose is about 5 mg per day or about 4 mg per day or about 3 mg per day or about 2 mg per day. In other embodiments, the administration of COMPOUND I or a pharmaceutically acceptable salt thereof is used to lower blood glucose levels. In still other embodiments, the subject is suffering from mild-to-moderate Alzheimer's disease. In other embodiments, a subject's blood glucose levels are lowered by at least 5 mg/dl, or at least 10 mg/dl, or at least 15 mg/dl, or at least 20 mg/dl or between 5 mg/dl to 20 mg/dl. In other embodiments, the subject's naïve glucose level is greater than 100 ng/dl.

In other embodiments, the administration of COMPOUND I or a pharmaceutically acceptable salt thereof is used to treat insomnia by the administration to a subject in need thereof of an amount less than 20 mg per day of COMPOUND I or a pharmaceutically acceptable salt thereof. COMPOUND I may be administered in a dose ranging from about 1 mg per day to less than 20 mg per day. In some embodiments, the dose is from about 1 mg per day to about 19 mg per day, or from about 1 mg per day to about 18 mg per day, or from about 1 mg per day to about 17 mg per day, or from about 1 mg per day to about 16 mg per day, or from about 1 mg per day to about 15 mg per day, or from about 1 mg per day to about 14 mg per day, or from about 1 mg per day to about 13 mg per day, or from about 1 mg per day to about 12 mg per day, or from about 1 mg per day to about 11 mg per day, or from about 1 mg per day to about 10 mg per day, or from about 1 mg per day to about 9 mg per day, or from about 1 mg per day to about 8 mg per day, or from about 1 mg per day to about 7 mg per day, or from about 1 mg per day to about 6 mg per day, or from about 1 mg per day to about 5 mg per day, or from about 1 mg per day to about 4 mg per day, or from about 1 mg per day to about 3 mg per day, or from about 1 mg per day to about 2 mg per day. In other embodiments, the dose is about 5 mg per day or about 4 mg per day or about 3 mg per day or about 2 mg per day. In other embodiments, the subject with from insomnia suffers from mild-to-moderate Alzheimer's disease. In other embodiments, the administration of COMPOUND I or a pharmaceutically acceptable salt thereof is used to decrease sleep onset latency. In still other embodiments, the subject with sleep onset latency also has mild-to-moderate Alzheimer's disease. In another embodiment, sleep onset latency is decrease by 1-5 minutes or by 5-10 minutes.

In some embodiments, treatment with COMPOUND I or a pharmaceutically acceptable salt thereof reduces the frequency of adverse events in a subject with mild-to-moderate Alzheimer's disease. In some embodiments, the adverse event may include falling, dizziness, confusional state, and somnolence. In other embodiments, the adverse events may be psychiatric adverse events. Psychiatric adverse events may include agitation, depression, anxiety, aggression, and restlessness. COMPOUND I or a pharmaceutically acceptable salt thereof may be administered in a dose ranging from about 1 mg per day to less than 20 mg per day. In some embodiments, the dose is from about 1 mg per day to about 19 mg per day, or from about 1 mg per day to about 18 mg per day, or from about 1 mg per day to about 17 mg per day, or from about 1 mg per day to about 16 mg per day, or from about 1 mg per day to about 15 mg per day, or from about 1 mg per day to about 14 mg per day, or from about 1 mg per day to about 13 mg per day, or from about 1 mg per day to about 12 mg per day, or from about 1 mg per day to about 11 mg per day, or from about 1 mg per day to about 10 mg per day, or from about 1 mg per day to about 9 mg per day, or from about 1 mg per day to about 8 mg per day, or from about 1 mg per day to about 7 mg per day, or from about 1 mg per day to about 6 mg per day, or from about 1 mg per day to about 5 mg per day, or from about 1 mg per day to about 4 mg per day, or from about 1 mg per day to about 3 mg per day, or from about 1 mg per day to about 2 mg per day. In other embodiments, the dose is about 5 mg per day or about 4 mg per day or about 3 mg per day or about 2 mg per day.

In any of the preceding embodiments, the administration of COMPOUND I or a pharmaceutically acceptable salt thereof may additionally include treatment with an acetylcholinesterase inhibitor (AChEI). The AChEI may include donepezil hydrochloride, galantamine hydrochloride, rivastigmine tartrate, or tacrine hydrochloride. In still other embodiments, the administration of COMPOUND I or a pharmaceutically acceptable salt thereof may additionally include treatment with memantine. In some embodiments, the subjects may have been receiving treatment with an AChEI or memantine for at least four months prior to the administration of COMPOUND I or a pharmaceutically acceptable salt thereof.

Another embodiment of the present invention includes a pharmaceutical composition including between 1 mg and 20 mg of COMPOUND I or a pharmaceutically acceptable salt thereof, and an AChEI. In other embodiments, the pharmaceutical composition may include between 1 mg and 20 mg of COMPOUND I or a pharmaceutically acceptable salt thereof, and memantine. The AChEI may include donepezil hydrochloride, galantamine hydrochloride, rivastigmine tartrate, or tacrine hydrochloride. In some embodiments, the AChEI is donepezil hydrochloride present between 5 mg and 23 mg. In other embodiments, the AChEI is galantamine hydrochloride present between 16 mg and 24 mg. In yet other embodiments, the AChEI is rivastigmine tartrate present between 6 mg and 12 mg. In still other embodiments, the AChEI is tacrine hydrochloride present at 40 mg. In still other embodiments, memantine is present between 5 mg and 20 mg. The pharmaceutical composition may include COMPOUND I from about 1 mg per day to about 19 mg per day, or from about 1 mg per day to about 18 mg per day, or from about 1 mg per day to about 17 mg per day, or from about 1 mg per day to about 16 mg per day, or from about 1 mg per day to about 15 mg per day, or from about 1 mg per day to about 14 mg per day, or from about 1 mg per day to about 13 mg per day, or from about 1 mg per day to about 12 mg per day, or from about 1 mg per day to about 11 mg per day, or from about 1 mg per day to about 10 mg per day, or from about 1 mg per day to about 9 mg per day, or from about 1 mg per day to about 8 mg per day, or from about 1 mg per day to about 7 mg per day, or from about 1 mg per day to about 6 mg per day, or from about 1 mg per day to about 5 mg per day, or from about 1 mg per day to about 4 mg per day, or from about 1 mg per day to about 3 mg per day, or from about 1 mg per day to about 2 mg per day.

In other embodiments, treatment with COMPOUND I or a pharmaceutically acceptable salt thereof reduces the amount of soluble $A\beta$ found in the cerebral spinal fluid (CSF). In some embodiments, the soluble form of $A\beta$ is isoform 1-40. In other embodiments, the soluble form of $A\beta$ is isoform 1-42. In still other embodiments, the soluble form of $A\beta$ is isoform 1-38. In still other embodiment, treatment with COMPOUND I or a pharmaceutically acceptable salt thereof alters the ratio between the amounts of isoform 1-40 to isoform 1-42 in the CSF.

In some embodiments, an observation was that when subjects in the 20-mg-dose group were discontinued from treatment, their ADAS-cog scores showed improvement. It is well known that Alzheimer's disease is a degenerative disease, and patients do not spontaneously remit. Exploratory analyses confirmed that subjects treated with 20 mg of COMPOUND I showed changes from baseline at endpoint visits (after treatment was stopped) that were superior to changes from baseline in the placebo group. This finding is consistent with the hypothesis that COMPOUND I had beneficial effects on the underlying disease state of the patients. The symptoms associated with higher concentrations of COMPOUND I, may have masked the improvement, and when the drug concentrations reduced to more beneficial ranges, the beneficial effects of the treatment could emerge.

EXAMPLES

Example 1

A Double-Blind, Placebo-Controlled, Randomized, Multicenter Study Evaluating the Efficacy and Safety of Eighteen Months of Treatment with COMPOUND I in Participants with Mild-to-Moderate Alzheimer's Disease The study was designed with three arms: 20 mg/day after a loading dose of 60 mg/day for 6 days; 5 mg/day after a loading dose of 15 mg/day for 6 days, and placebo. The study randomized N=399 patients with mild-moderate Alzheimer's disease in balanced ratios (1:1:1). The 20-mg-dose group was terminated at an interim analysis. Subsequently, the study was terminated prematurely based on a futility analysis that was planned in the original protocol.

Statistical analysis of the study included analyses that were planned in the protocol and statistical analysis plan and also exploratory and investigative analyses. Subsequent to a patient's termination of study treatment, the patient was instructed to continue attending study visits, and data continued to be collected. Statistical analysis included datasets that included all available data (on-treatment and off-treatment) and on-treatment data, where "on-treatment" was defined as within 28 days of the date of last dose. Off-treatment data reflect the treatment that was given according to the randomization schedule; therefore, on-treatment and off-treatment analyses that are based on the randomized population and follow the intent-to-treat principles are valid.

Statistical analysis compared the 5-mg-dose group (n=131; mean age=74 yr; 53% female) with the placebo group (n=132; mean age 72 yr; 57% female). Dropout rates in the incomplete study were 48% and 52% for 5 mg COMPOUND I and placebo, respectively. Performing a standard intent-to-treat analysis of covariance (adjusting for baseline) on change from baseline to endpoint in ADAS-cog using last-observation-carried-forward on all randomized patients with on-treatment data resulted in least-squares means of 6.4 and 8.7 (nominal p=0.03). Actual mean changes from baseline were 6.59 (SD=7.91) and 9.00 (SD=9.21) for groups dosed with 5 mg COMPOUND I and placebo, respectively. The unadjusted analysis likewise yielded nominal p=0.03 favoring treatment with 5 mg COMPOUND I.

Additional analysis on observed cases by visit, on percent change from baseline in ADAS-cog, and proportion of patients showing an increase in ADAS-cog of 7 or more points (responder analysis) likewise had nominal p-values favoring 5-mg COMPOUND I over placebo at the trend level or better.

The following table summarizes the planned efficacy analysis designated as primary and the supportive analyses to ensure robustness of the conclusions of the primary analysis. These analyses were planned in the study protocol, planned in the statistical analysis plan, and follow the intent-to-treat principles depicted in ICH E9. A summary of the key results on ADAS-cog at 18 months follows:

TABLE 1

Summary of planned ITT statistical analysis described in the study protocol

| Analysis | Statistic | Treatment Group | | Statistical Analysis | |
| --- | --- | --- | --- | --- | --- |
| | | 5-mg dose COMPOUND I | Placebo | Methodology | p-value |
| Primary analysis described in protocol and SAP: mITT Report number: 2011-06-23-001 | Sample size | 69 | 68 | ANCOVA with MI imputation (primary in protocol and SAP) | 0.008 |
| | Mean change to month 18 | 8.84 | 11.94 | Complete Cases ANCOVA | 0.02 |
| | Median change to month 18 | 6.76 | 10.34 | LOCF ANCOVA | 0.03 |
| | Delta in mean | 3.1 | | GEE | 0.03 |
| | Delta in median | 3.58 | | Mixed models repeated measures (random effects) | 0.04 |

Example 2

Drug Effects were More Pronounced Among Patients Who Presented with Less Severity of Alzheimer's Disease than Those Who Presented with Greater Severity of Alzheimer's Disease, Based on the ADAS-Cog at Baseline Entry into the study was based on the MMSE; there was no eligibility criterion based on the ADAS-cog. Post-hoc analysis examined characteristics of individuals who may have more pronounced benefit than others. Discriminant analysis suggested that some subgroups of patients may respond better than others to COMPOUND I.

An observation of the analysis revealed that patients in Study who presented with less severe Alzheimer's showed better delineation from placebo than those who had more severe disease at entry, based on the ADAS-cog.

FIG. 1 displays the change from baseline in ADAS-cog for an ADAS-cog subgroup of subjects presenting with ADAS-cog scores at baseline of less than or equal to 23.

The subjects presenting with mild dementia treated with placebo (dashed line) show greater increases from baseline in ADAS-cog, indicating worsening of Alzheimer's disease at a greater rate than subjects presenting with mild Alzheimer's disease who were treated with 5-mg COMPOUND I (solid line). The sample size varies over time as patients leave the study. This analysis includes all data on-treatment where on-treatment is defined as date of last dose plus 28 days. The difference between the placebo group and the group treated with COMPOUND I at 5 mg is statistically significant at Month 18 using last-observation-carried-forward to accommodate missing data.

A responder is one who has not progressed, and progression is an increase of 7 or more points on the ADAS-cog within 18 months.

Figure 2:
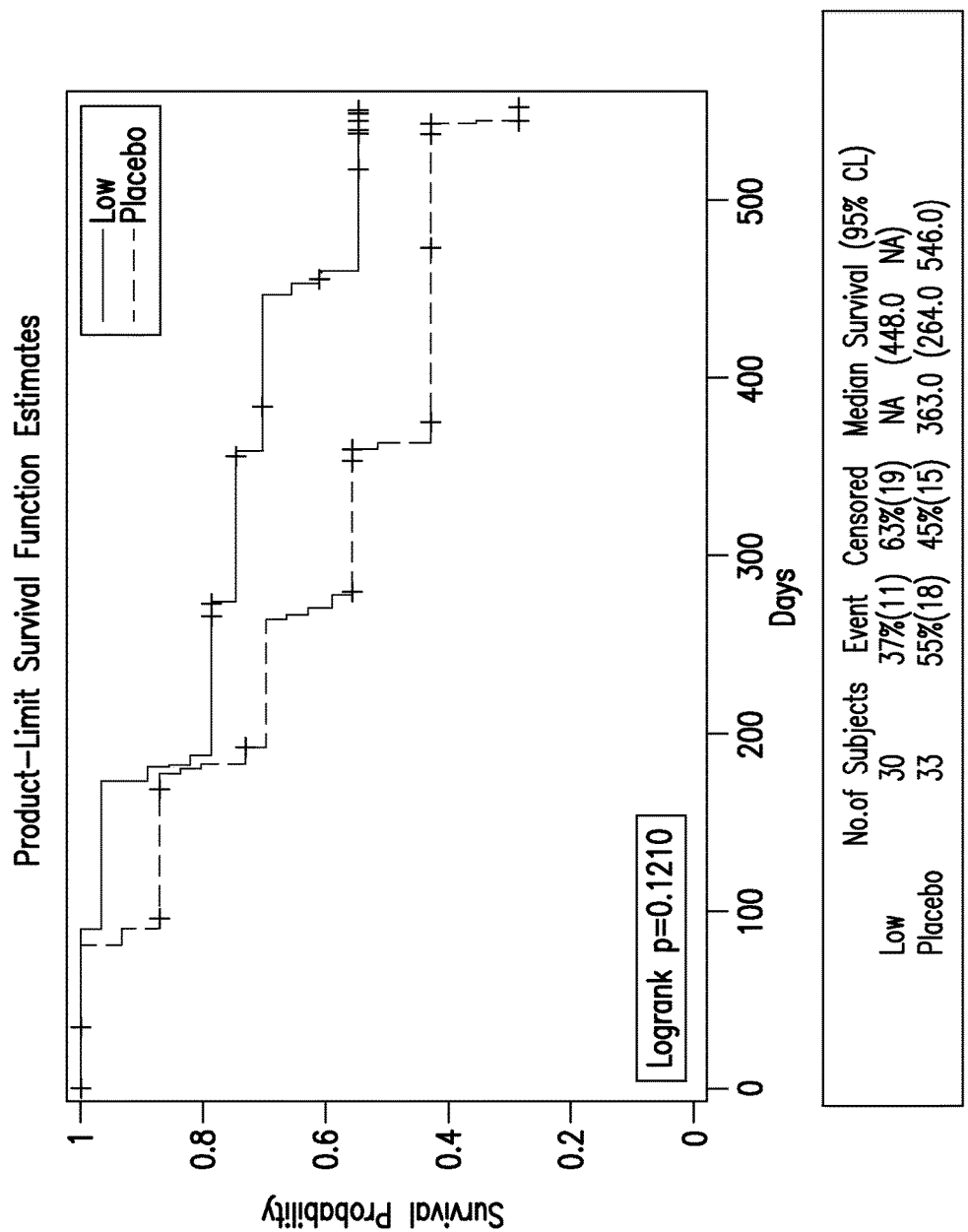
FIG. 2—Kaplan-Meier curves for the group dosed with placebo and the group dosed with 5 mg of COMPOUND I where an event is defined as achievement of an increase in ADAS-cog of 7 or more points at any time for the subgroup of subjects with low baseline ADAS-cog at presentation where low is among subjects in the lowest 25% of the study population.

FIG. 2 displays Kaplan-Meier curves for the group dosed with placebo and the group dosed with COMPOUND I at 5 mg where an event is defined as achievement of an increase in ADAS-cog of 7 or more points at any time. The Kaplan- Meier curves in FIG. 2 show the proportions of subjects declining in Alzheimer's disease as measured by the ADAS-cog by classifying a subject as having an "event" at the time of an increase in ADAS-cog of 7 points (reference for 7 points being progression: Publication by Vellas, et al., "Long-term changes in ADAS-cog: What is clinically relevant for disease modifying trails in Alzheimer?" (Volume 11, Number 4, 2007; *Journal of Nutrition, Health & Aging*)). The analysis uses Markov-Chain model conventions with achievement of an event as an absorbing state. The low dose group (5 mg, indicated by the solid line) dominates the placebo group (indicated by the dotted line) at all points, and the distance between the lines indicates superiority of treatment with COMPOUND I relative to placebo to retard the progression of Alzheimer's disease in patients who present with mild Alzheimer's disease at baseline.

Example 3

Drug Effects were More Pronounced Among Patients with Concentrations within Identified Ranges Concentration levels were highly correlated with bodyweight and with BMI. The optimal dosing paradigm is concentration-driven.

Blood samples were taken at each study visit to measure trough concentrations of drug levels. Analysis of drug concentrations correlated with response as assessed by ADAS-cog. Statistical modeling to identify the concentration range that optimizes the efficacy of the compound was done using the trough concentrations and the change from baseline in ADAS-cog. Preliminary results showed a range of 7-20 ng/ml where COMPOUND I-treated subjects had maximal response (smallest changes from baseline in ADAS-cog) among all other groups in the study. Other analyses resulted in a range of 8 to 15 ng/ml. When analysis was expanded to include 4 supportive efficacy measures in addition to the ADAS-cog, (MMSE, ADL, CDR-sb, and NPI), the identified optimal range was 8-13 ng/ml.

For analysis, subjects were categorized into exposure groups by the maximum of the trough levels during the 18-month trial period. Analysis using tertile cuts, quartile cuts, quintile cuts, and decile cuts were consistent. PK/PD modeling is ongoing to identify an optimal dosing paradigm.

Figure 3:
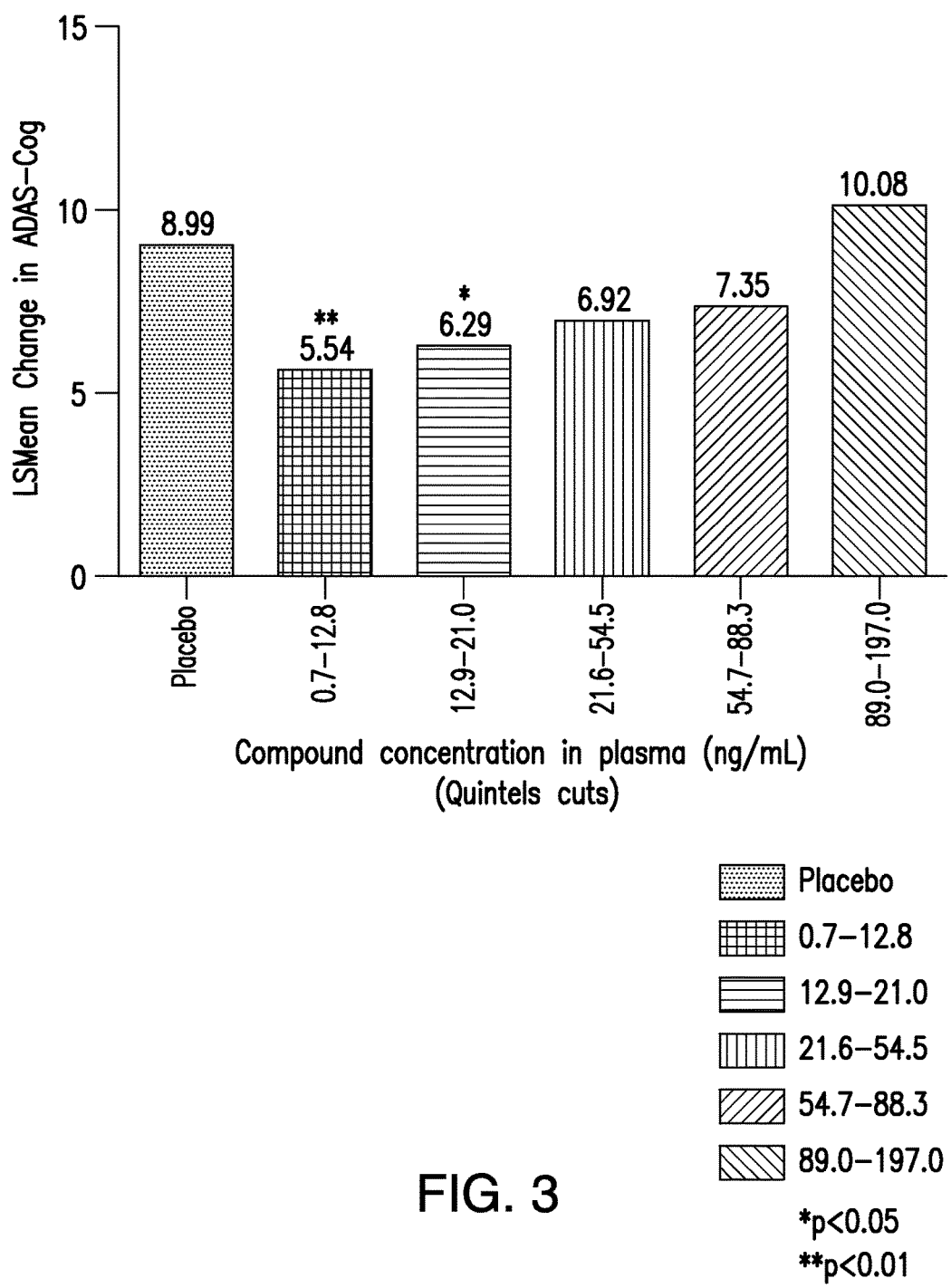
FIG. 3—Graph showing concentration-driven classification of subjects regardless of dose of COMPOUND I administered.

FIG. 3 displays bar graphs showing concentration-driven classification of subjects regardless of dose administered. In FIG. 3, it is shown that concentrations in the range of 0.7 to 12.8 ng/ml show a nominally statistically significant difference from placebo in the LOCF LSMEAN change from baseline in ADAS-cog, where higher scores indicate more advanced Alzheimer's disease. The concentration range in the third bar, which is for pk concentrations of 12.9 to 21.0 ng/ml, is also statistically superior to placebo in delaying the progression of Alzheimer's disease. A conclusion of the analysis is that when subjects are dosed with COMPOUND I at either 5 mg or 20 mg and have a resulting concentration in the range from 8 to 13 ng/ml, inclusive, the superiority of COMPOUND I over placebo is evident.

The efficacy of COMPOUND I is more pronounced in Alzheimer's disease when the dosing paradigm is concentration-driven than when fixed dosing is used. Analysis shows that if the concentrations are too low, the efficacy is not evident. However, if the concentrations are too high, it appears that efficacy may be masked by side effects. When the concentrations are in the target interval, the superiority of COMPOUND I over placebo is evident.

Figure 4:
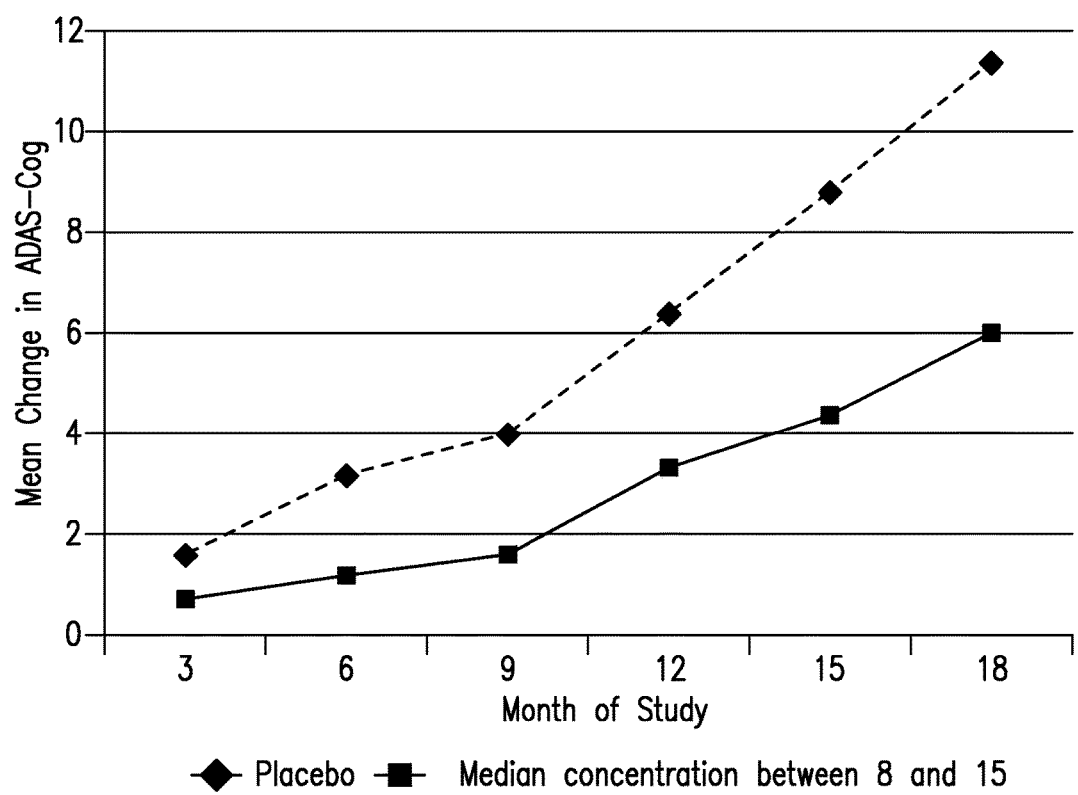
FIG. 4—Graph showing profile over time comparing placebo-treated subjects to subjects in study whose measured median pk concentrations were in the range of 8 to 15 ng/ml of COMPOUND I.
Figure 5A:
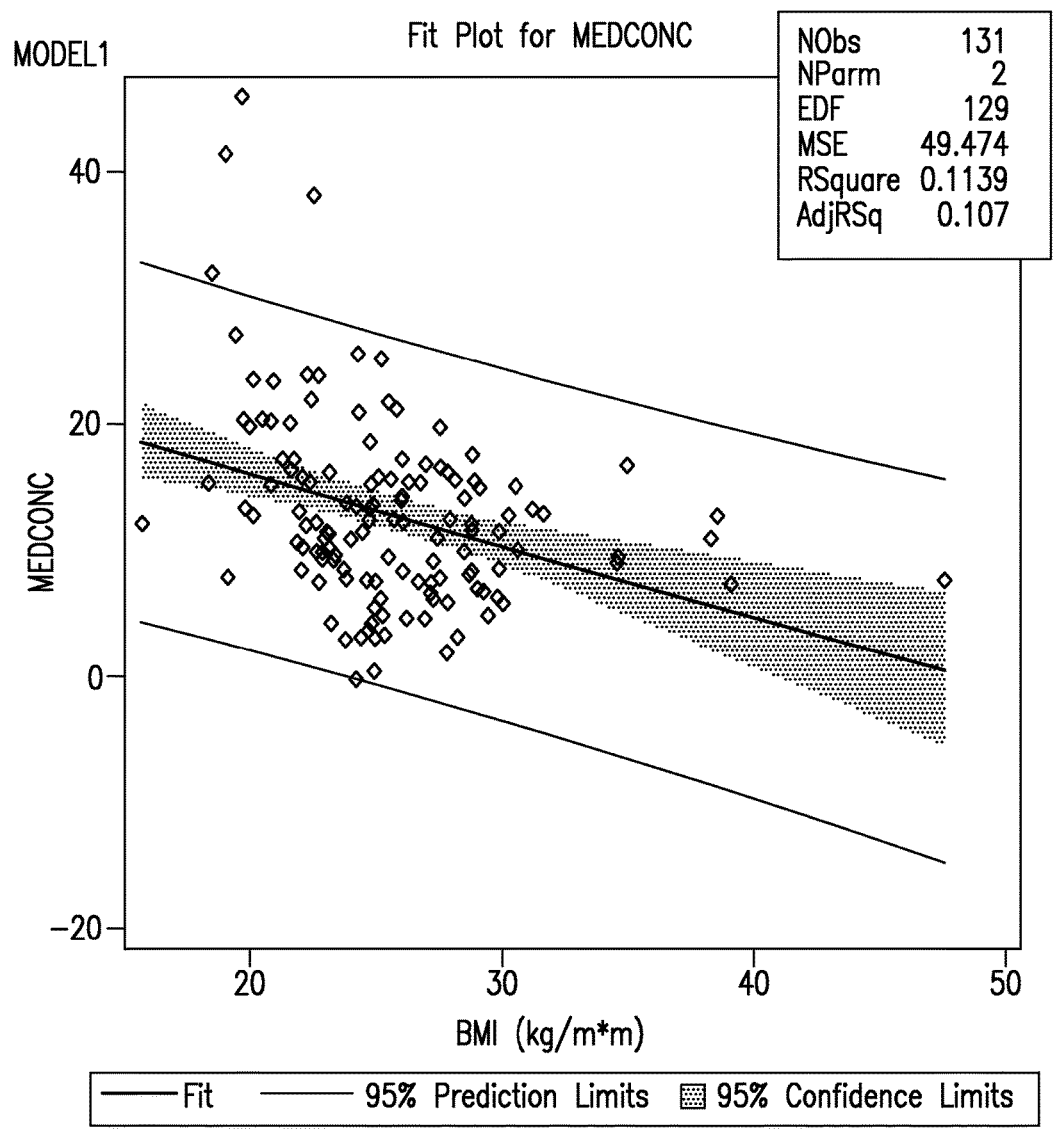
FIG. 5a—Graph showing a regression analysis regressing concentration (ng/ml) on BMI ($kg/m^2$) for the 5 mg dose group.
Figure 5B:
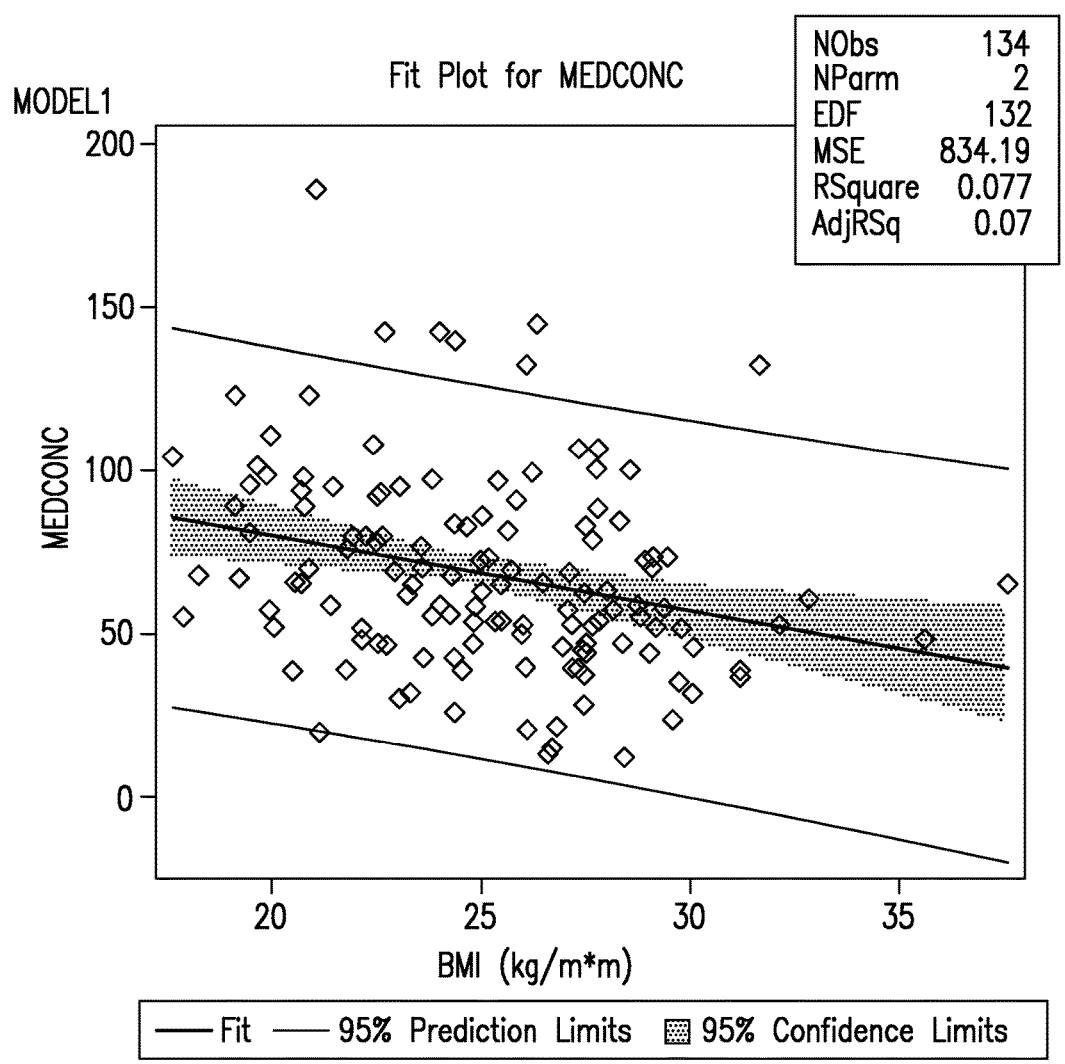
FIG. 5b—Graph showing a regression analysis regressing concentration (ng/ml) on BMI ($kg/m^2$) for the 20 mg dose group.
Figure 5C:
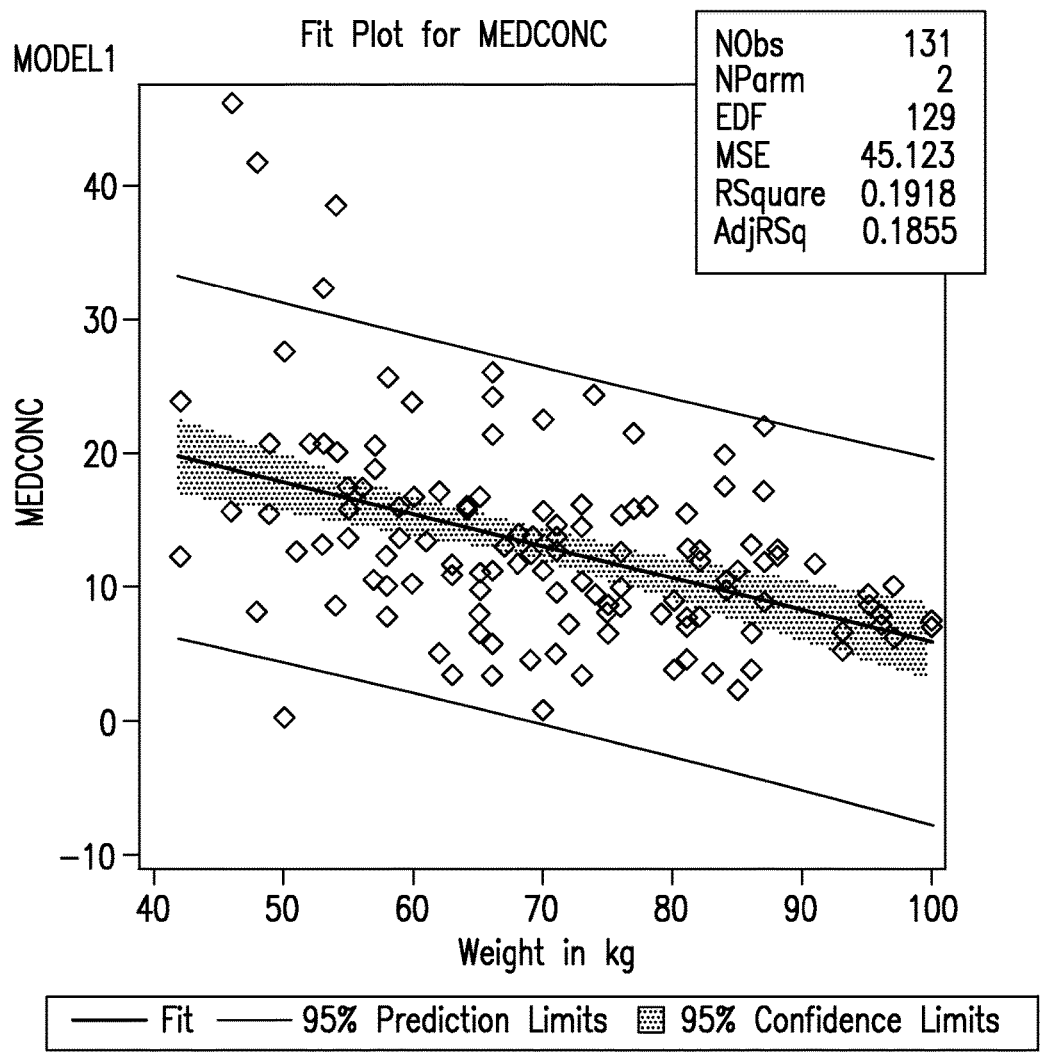
FIG. 5c—Graph showing a regression analysis regressing concentration (ng/ml) on body weight (kg) for the 5 mg dose group.
Figure 5D:
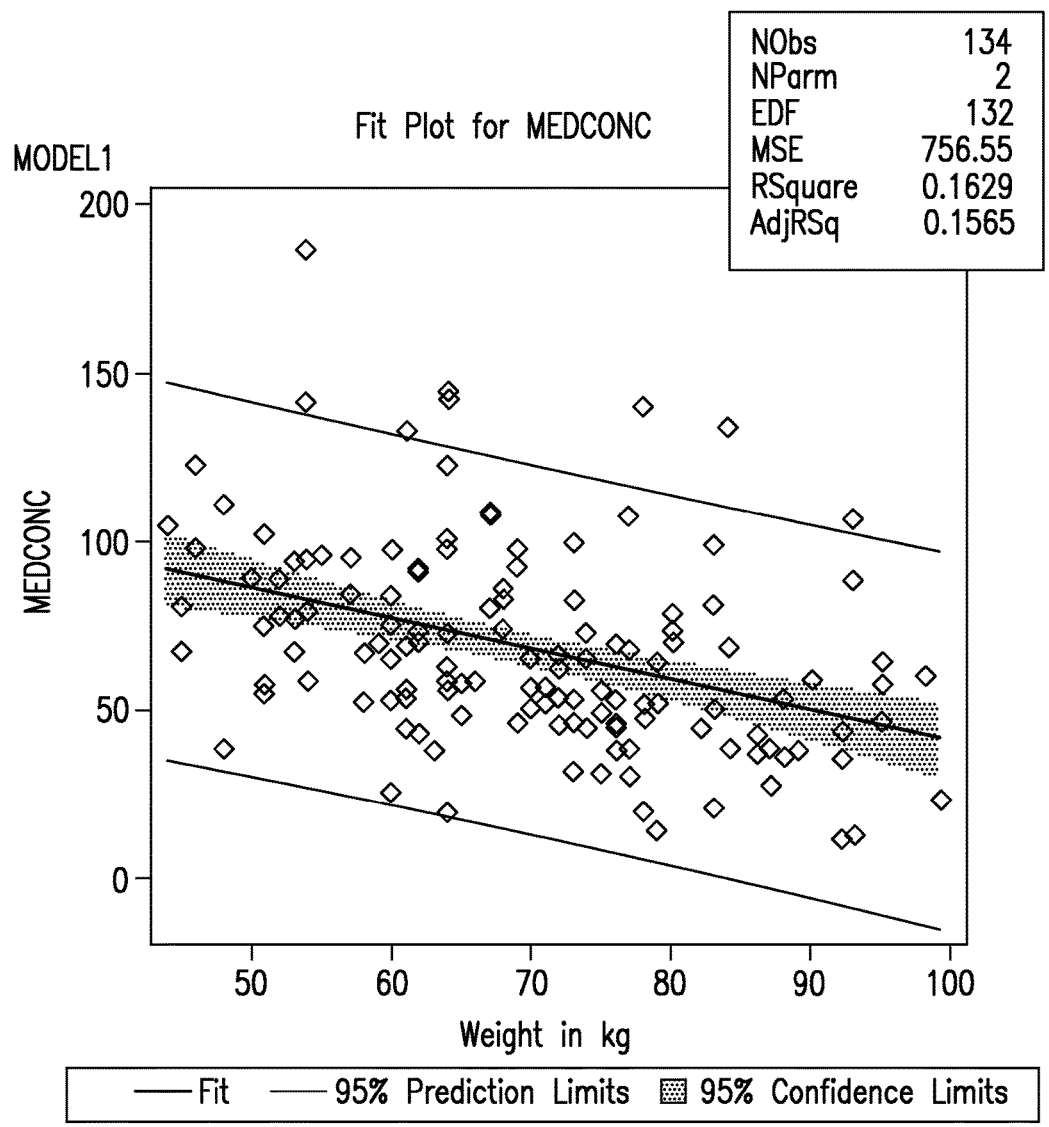
FIG. 5d—Graph showing a regression analysis regressing concentration (ng/ml) on body weight (kg) for the 20 mg dose group.
Figure 6A:
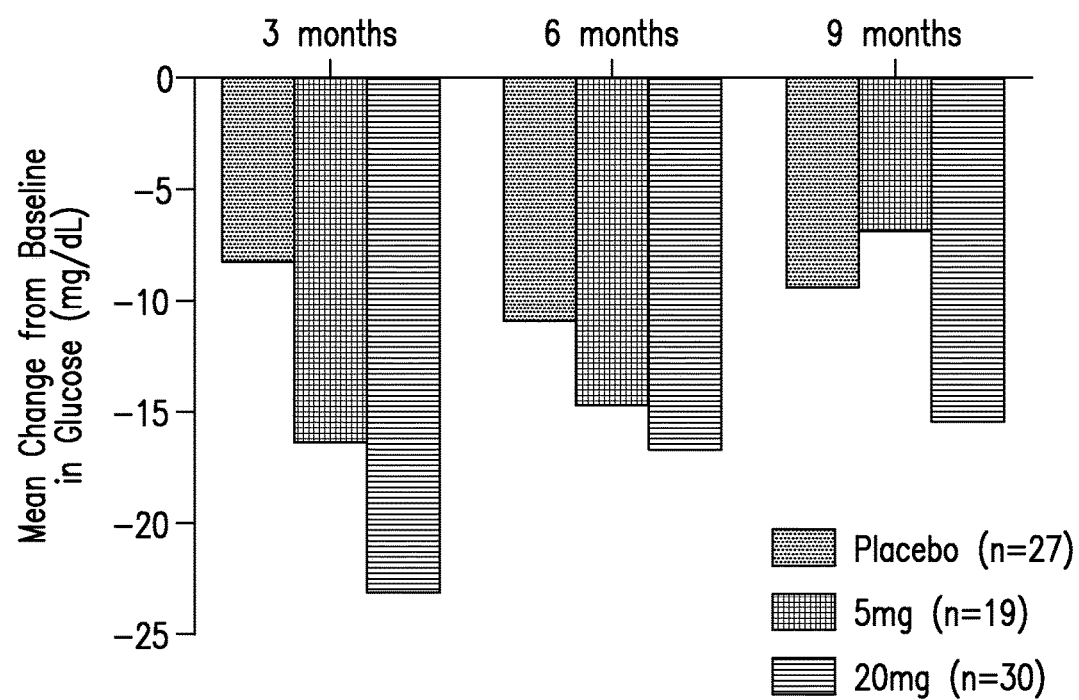
FIG. 6a—Graph showing that mean change from baseline in glucose for subjects who present with high glucose values where high is defined as being 100 mg/ml or greater at baseline. It is noted that comparison with placebo rules out regression to the mean.
Figure 6B:
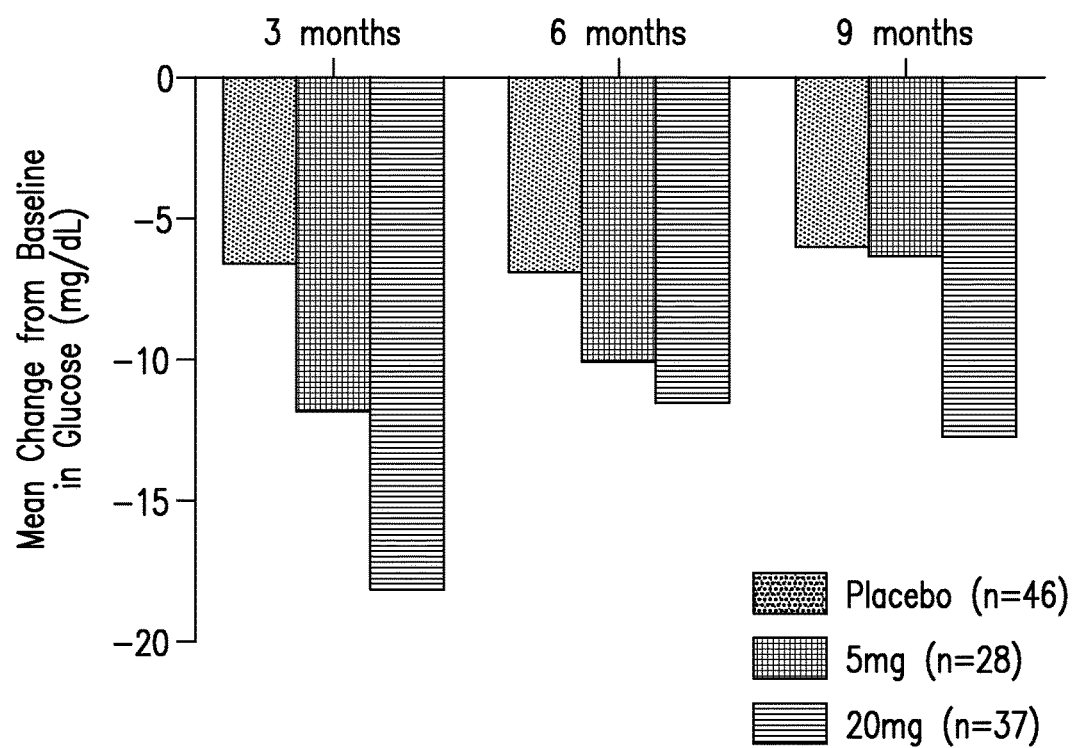
FIG. 6b—Graph showing that mean change from baseline in glucose for subjects who present with high glucose values where high is defined as being in the highest one third (33%) of glucose values at baseline. It is noted that comparison with placebo rules out regression to the mean.
Figure 6C:
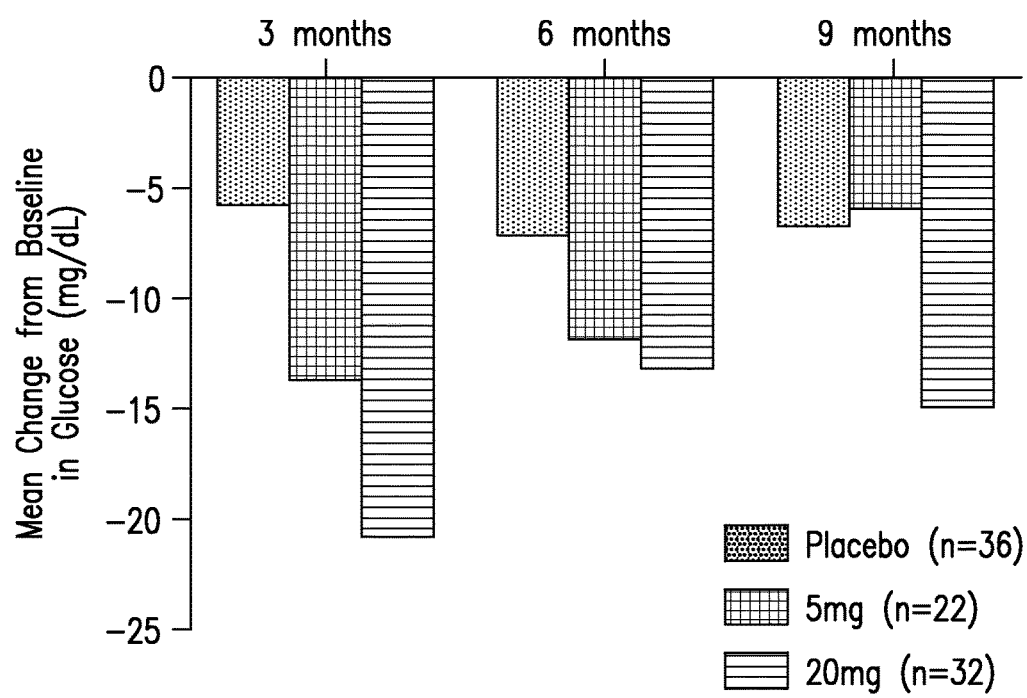
FIG. 6c—Graph showing that mean change from baseline in glucose for subjects who present with high glucose values where high is defined as being in the highest 25% of glucose values at baseline. It is noted that comparison with placebo rules out regression to the mean.
Figure 6D:
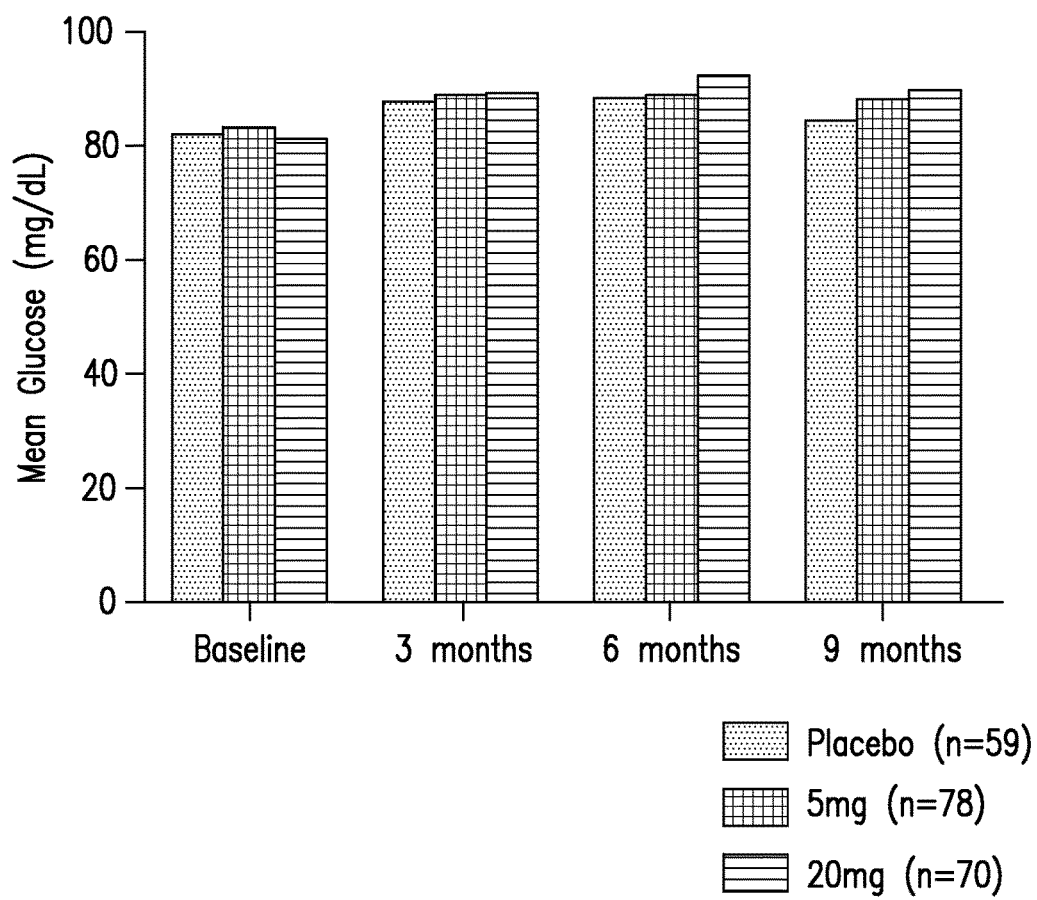
FIG. 6d—Graph showing that mean glucose for subjects who present with normal or low glucose values where subgroup is taken as all subjects in the lower half (50%) of glucose values at baseline (subgroup is defined with a median cut).

FIG. 4 shows line graphs of the profile over time comparing placebo-treated subjects to subjects in the study whose measured median pk concentrations were in the range 8 to 15 ng/ml. The subjects treated with placebo (dashed line) show greater increases from baseline in ADAS-cog, indicating worsening of Alzheimer's disease at a greater rate than subjects who were treated with COMPOUND I with median pk concentrations in the range of 8 and 15 ng/ml (solid line). The sample size varies over time as patients leave the study. This analysis includes all data on-treatment where on-treatment is defined as date of last dose plus 28 days. The difference between the placebo group and the group treated with COMPOUND I these concentrations has nominal statistical significance at Month 18 using last-observation-carried-forward to accommodate missing data.

Table 2 provides a summary of statistics delineating between placebo and treatment with COMPOUND I beginning with Month 6 and being maintained over the course of the remainder of the 18-month study.

TABLE 2

Summary of Mean and Median changes in ADAS-cog over time for subjects treated with placebo and those treated with COMPOUND I with median trough concentrations between 8 and 15 ng/ml.

| Time | Statistic | Placebo | Concentration between 8 and 15 ng/ml | Mean Difference | P-value (2-sample t-test) |
|---|---|---|---|---|---|
| Base-line | Mean | 24.11 | 24.22 | 0.11 | 0.9 |
|  | Median | 22.3 | 22.0 |  |  |
| 3 | Mean change | 1.57 | 0.73 | 0.84 | 0.3 |
|  | Median change | 2.0 | 2.3 |  |  |
| 6 | Mean change | 3.16 | 1.16 | 2.00 | 0.03 |
|  | Median change | 2.7 | 1.3 |  |  |
| 9 | Mean change | 3.95 | 1.52 | 2.43 | 0.04 |
|  | Median change | 2.2 | 1.3 |  |  |
| 12 | Mean change | 6.34 | 3.31 | 3.03 | 0.02 |
|  | Median change | 5.5 | 2.3 |  |  |
| 15 | Mean change | 8.74 | 4.39 | 4.35 | 0.008 |
|  | Median change | 7.8 | 4.7 |  |  |
| 18 | Mean change | 11.32 | 6.04 | 5.28 | 0.01 |
|  | Median change | 10.3 | 4.7 |  |  |

The data in Table 2 shows that treatment with COMPOUND I in subjects whose measured median trough concentrations are between 8 and 15 ng/ml are statistically delineated with nominal statistical significance beginning at Month 6. Analysis conclusions indicate that, in certain concentration ranges, the benefits of treatment with COMPOUND I are clear. Analysis of variations in concentrations resulted in conclusions that bodyweight and BMI affected concentrations. These analyses support the need for concentration-driven treatment that incorporates bodyweight or BMI.

FIG. 5 shows the regression analysis regressing concentration on BMI. Regression analysis regressing concentration (dependent variable) onto BMI and onto bodyweight showed statistically significant negative correlations in all 4 analyses: subjects who have lower bodyweight or lower BMI tend to have higher concentration values for the same administered dose than subjects who have higher bodyweight or higher BMI values. The result was true for each dose level; therefore, the finding applies to both dose levels. These analyses are based on all available on-treatment where on-treatment is defined as date of last dose plus 28 days. This finding translates to a dosing paradigm that incorporates bodyweight or BMI in the dose administered to produce the desired concentration levels. These findings are consistent with claims that concentration drives efficacy and bodyweight or BMI drives concentration. This finding suggests that at low bodyweight and low BMI, lower doses are likely to be more effective than higher doses.

Example 4

Decreases in Glucose are Observed when Treated with COMPOUND I at High Doses when Subjects Present with Elevated Glucose Values Statistical analysis of data from the study with COMPOUND I concluded that there were declines in glucose values, particularly for subjects entering the studies with elevated glucose levels. Lowering elevated glucose benefits patients, while lowering normal or lower level glucose values could have a detrimental effect.

Statistical analysis showed that in the study, subjects who presented with higher glucose values had declines when treated with 20 mg of COMPOUND I compared with placebo. Subjects with lower glucose values at baseline did not show significant decreases in glucose.

FIG. 6a-d demonstrates the mean change from baseline in glucose is displayed by treatment group using all data available at Months 3, 6, and 9. Subgroups were defined by taking all subjects with a baseline value of 100 mg/dl or greater, all subjects in the upper third (tertile cut), all subjects in the uppermost 25% (quartile cut), and all subjects in the uppermost 20% (quintile cut (not shown)). FIG. 6-d displays subjects with lower or normal values, where the subgroup is defined by a group median cut, and the subgroup is all subjects with baseline values less than the group median (lower half). After Month 9, withdrawal rates resulted in data too sparse for meaningful analysis. The group treated with high-dose (20 mg) of COMPOUND I showed marked declines in glucose which were statistically significant within the treatment group ($p<0.05$) and also statistically significantly different from placebo using 2-sample t-tests ($p<0.05$). For subjects who are normal or have low baseline glucose values, there is not a decline associated with treatment with COMPOUND I. The differences among treatment groups at baseline are not statistically significant. Comparisons investigating the decreases in glucose associated with treatment with COMPOUND I in the subgroups of subjects who presented into the study with glucose values below the population median for the study are not statistically significant ($p>0.15$).

Example 5

Treatment with 5 Mg Compound I Delays or Reduces the Incidence of Adverse Events Adverse Events Adverse events of special interest (AESI) were related to potential cognitive impairment: fall, dizziness, confusional state, and somnolence. Reported frequencies for at least one AESI for the groups treated with 20 mg, 5 mg, and placebo, respectively, were 50 (37%), 49 (37%), and 44 (33%). Specific AESI showed no discernible pattern related to dose of COMPOUND I.

Figure 7:
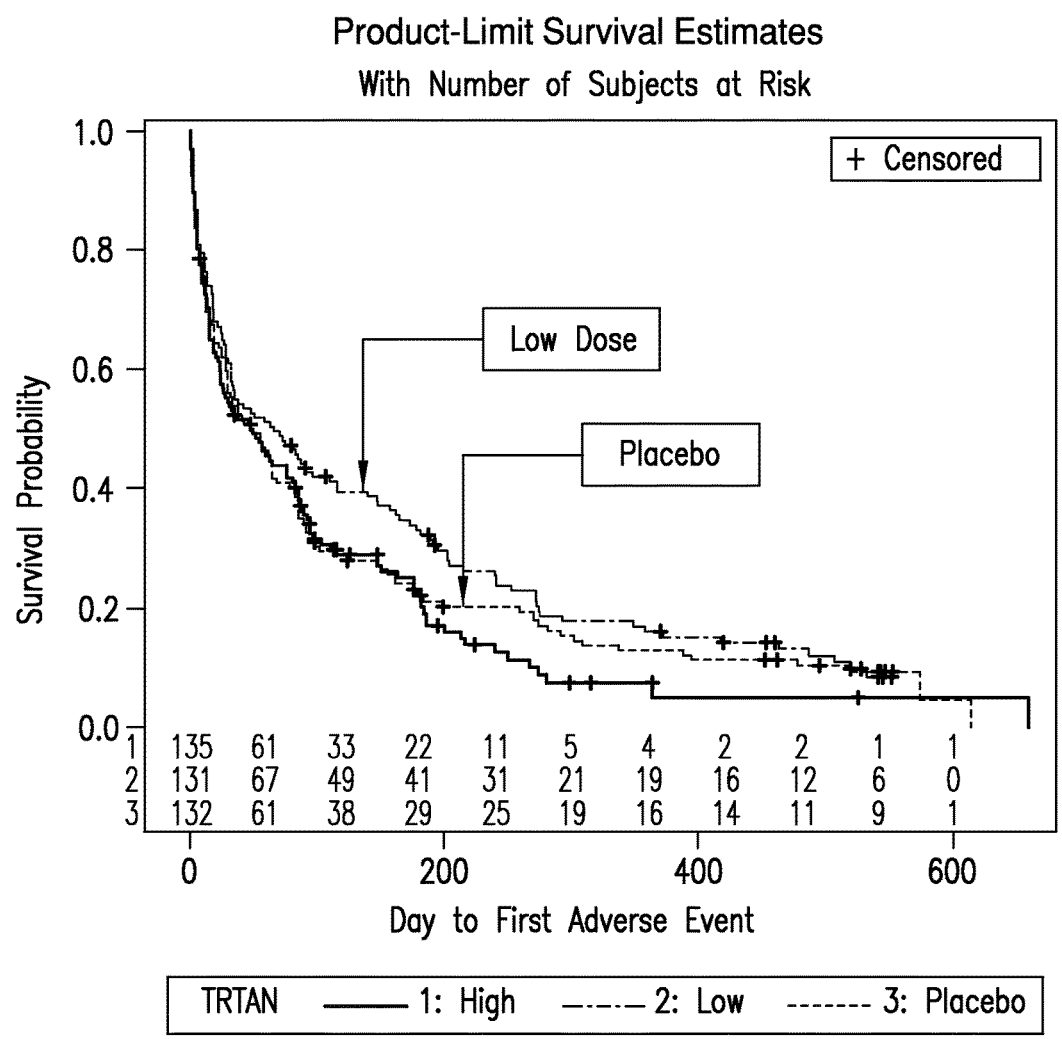
FIG. 7—Kaplan-Meier curves are shown of time for adverse event by dose group.

FIG. 7 displays Kaplan-Meier curves for time to event for adverse event by dose group.

FIG. 7 shows the time to event curves display the proportions of subjects event-free by study day with Kaplan-Meier censoring when subjects withdraw from the study event-free. The analysis uses Markov-Chain model conventions with achievement of an event as an absorbing state. The low dose group dominates the placebo group at all points, and the distance between the lines indicates benefit of treatment with COMPOUND I at 5 mg relative to placebo to reduce the likelihood of having an adverse event.

Figure 8:
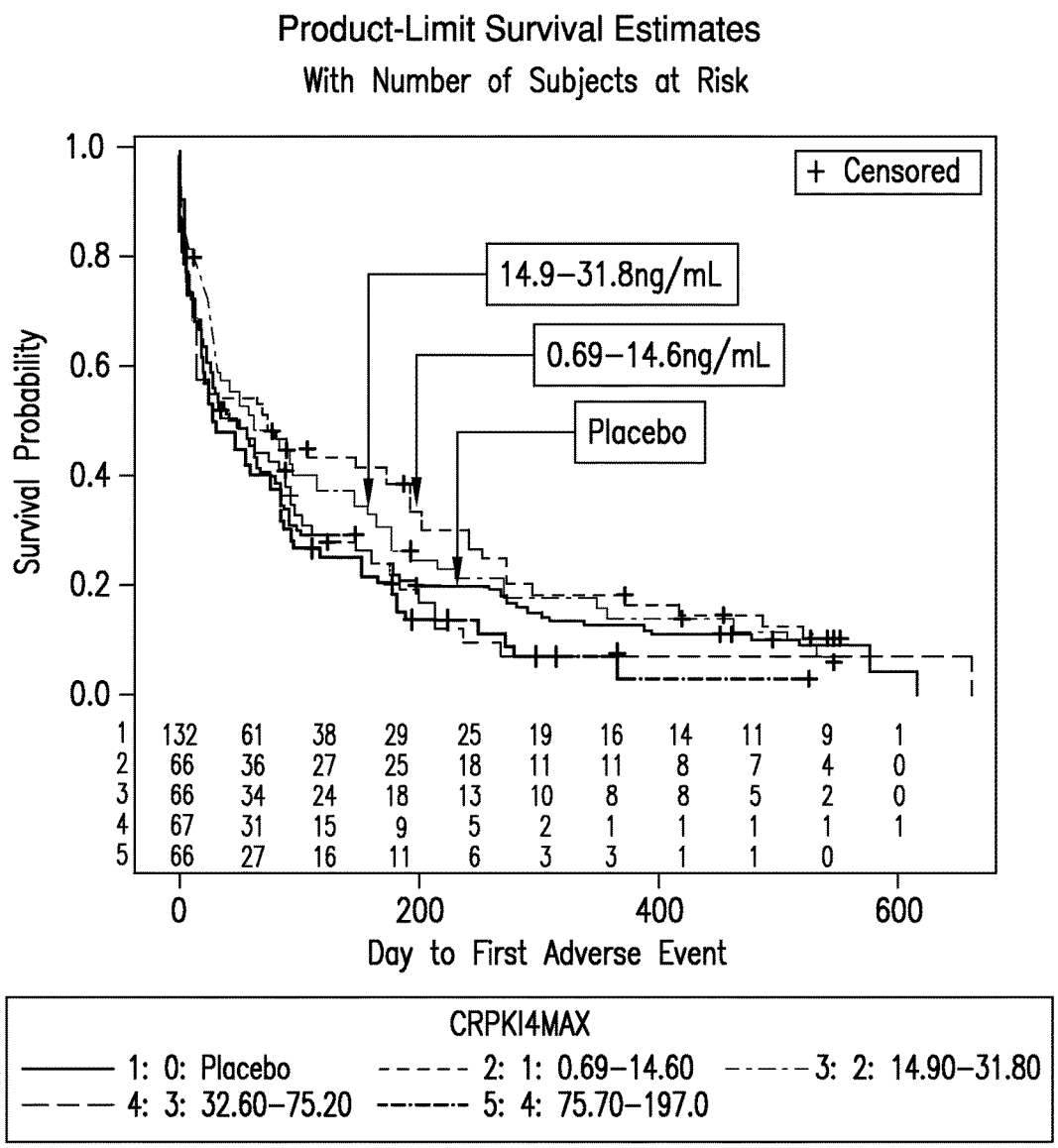
FIG. 8—Kaplan-Meier curves are shown of time for adverse event by concentration group.

FIG. 8 displays Kaplan-Meier curves for time to event for adverse event by concentration group. The time to event curves display the proportions of subjects event-free by study day with Kaplan-Meier censoring when subjects withdraw from the study event-free. The analysis uses Markov-Chain model conventions with achievement of an event as an absorbing state. The group with concentrations less than 14.6 ng/dl (indicated by the dashed line) dominates the placebo group (indicated by the solid line) at all points after month 3, and the distance between the lines indicates benefit of treatment with COMPOUND I at low concentrations relative to placebo to reduce the likelihood of having an adverse event.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the present invention.

We claim:

1. A method of treating Alzheimer's disease comprising administering to a human in need thereof an amount of about 5 mg per day of [3-(4-{2-butyl-1-[4-(4-chloro-phenoxy)-phenyl]-1H-imidazol-4-yl}-phenoxy)-propyl]-diethyl amine, wherein the human is suffering from mild Alzheimer's disease.

2. The method of claim 1, wherein the method of treatment further comprises administering to the human an acetylcholinesterase inhibitor (AChEI).

3. The method of claim 1, wherein the method of treatment further comprises administering to the human memantine hydrochloride.

4. The method of claim 1, wherein the treatment is determined by the improvement, or no deterioration, or a reduction in the rate of deterioration in at least one of the assessments selected from the group consisting of the Alzheimer's Disease Assessment Scale-cognitive subscale (ADAS-cog), the Clinical Dementia Rating Sum of Boxes (CDR-sb), the Alzheimer's Disease Cooperative Study Activities of Daily Living Scale (ADCS-ADL), the Neuropsychiatric Inventory (NPI), and the Mini-Mental State Examination (MMSE).

5. The method of claim 1, wherein the human suffering from mild Alzheimer's disease presents with an ADAS-cog score of less than or equal to 23.

6. The method of claim 2, wherein the AChEI is selected from the group consisting of donepezil hydrochloride, galantamine hydrochloride, rivastigmine tartrate, and tacrine hydrochloride.

7. The method of claim 6, wherein the AChEI is donepezil hydrochloride, and wherein the donepezil hydrochloride is administered in an amount between 5 mg and 23 mg per day.

8. The method of claim 6, wherein the AChEI is galantamine hydrochloride, and wherein the galantamine hydrochloride is administered in an amount between 16 mg to 24 mg per day.

9. The method of claim 6, wherein the AChEI is rivastigmine tartrate, and wherein the rivastigmine tartrate is administered in an amount between 6 mg to 12 mg per day.

10. The method of claim 6, wherein the AChEI is tacrine hydrochloride, and wherein the tacrine hydrochloride is administered in an amount of 40 mg per day.

11. The method of claim 3, wherein the memantine hydrochloride is administered in an amount between 5 mg to 20 mg per day.

12. The method of claim 1, wherein the human suffering from mild Alzheimer's disease presents with a Mini-Mental State Examination score of greater than or equal to 21.

13. The method of claim 1, wherein the human suffering from mild Alzheimer's disease presents with a Mini-Mental State Examination score of between about 21 to 26.

14. The method of claim 4, wherein the treatment results in a reduction in the rate of deterioration in at least one of the assessments selected from the group consisting of the Alzheimer's Disease Assessment Scale-cognitive sub scale (ADAS-cog), the Clinical Dementia Rating Sum of Boxes (CDR-sb), the Alzheimer's Disease Cooperative Study Activities of Daily Living Scale (ADCS-ADL), the Neuropsychiatric Inventory (NPI), and the Mini-Mental State Examination (MMSE).

15. The method of claim 4, wherein the treatment results in a reduction in the rate of deterioration in ADAS-cog scores.

16. The method of claim 15, wherein the treatment results in a median reduction in the rate of deterioration of ADAS-cog scores of two to five points.

17. The method of claim 15, wherein treatment results in a mean reduction in the rate of deterioration of ADAS-cog scores of 3.1.

18. The method of claim 1, wherein the [3-(4-{2-butyl-1-[4-(4-chloro-phenoxy)-phenyl]-1H-imidazol-4-yl}-phenoxy)-propyl]-diethyl amine is administered orally.

19. A method of treating mild dementia of Alzheimer's type in a human comprising administering to the human an oral dose of 5 mg of [3-(4-{2-butyl-1-[4-(4-chloro-phenoxy)-phenyl]-1H-imidazol-4-yl}-phenoxy)-propyl]-diethyl amine once daily.

20. The method of claim 19, wherein the human presents with a Mini-Mental State Examination (MMSE) score of between about 21 to 26.

21. A method of using a receptor for advanced glycation end-products antagonist for treating mild dementia of Alzheimer's type in a human comprising administering to the human an oral dose of 5 mg of [3-(4-{2-butyl-1-[4-(4-chloro-phenoxy)-phenyl]-1H-imidazol-4-yl}-phenoxy)-propyl]-diethyl amine once daily.

22. The method of claim 21, wherein the human presents with a Mini-Mental State Examination (MMSE) score of between about 21 to 26.

* * * * *

UNITED STATES PATENT AND TRADEMARK OFFICE
CERTIFICATE OF CORRECTION

PATENT NO. : 9,717,710 B2
APPLICATION NO. : 14/059529
DATED : August 1, 2017
INVENTOR(S) : Orlandi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this
Twelfth Day of November, 2024

Katherine Kelly Vidal
*Director of the United States Patent and Trademark Office*